United States Patent
Lopes Carvalho et al.

(10) Patent No.: US 11,493,516 B2
(45) Date of Patent: *Nov. 8, 2022

(54) BIOMARKERS FOR ASSESSING BREAST CANCER

(71) Applicant: METABOLOMYCS, INC, Long Beach, CA (US)

(72) Inventors: Andre Lopes Carvalho, Barretos (BR); Rene Aloisio Da Costa Vieira, Barretos (BR); Ismael Dale Cotrim Guerreiro Da Silva, Sao Paulo (BR); Edson Guimaraes Lo Turco, Sao Paulo (BR); Therese Koal, Innsbruck (AT)

(73) Assignee: Metabolomycs, Inc, Long Beach, CA (US)

( * ) Notice: Subject to any disclaimer, the term of this patent is extended or adjusted under 35 U.S.C. 154(b) by 57 days.

This patent is subject to a terminal disclaimer.

(21) Appl. No.: 17/196,164

(22) Filed: Mar. 9, 2021

(65) Prior Publication Data

US 2021/0190785 A1    Jun. 24, 2021

Related U.S. Application Data

(63) Continuation of application No. 15/510,080, filed as application No. PCT/EP2015/070752 on Sep. 10, 2015, now Pat. No. 10,962,542.

(30) Foreign Application Priority Data

Sep. 10, 2014    (EP) ................................... 14184200

(51) Int. Cl.
| | | |
|---|---|---|
| *G01N 33/574* | (2006.01) | |
| *G01N 33/68* | (2006.01) | |
| *G01N 33/92* | (2006.01) | |
| *A61B 5/00* | (2006.01) | |

(52) U.S. Cl.
CPC ......... *G01N 33/57415* (2013.01); *A61B 5/41* (2013.01); *G01N 33/57484* (2013.01); *A61B 5/00* (2013.01); *G01N 33/6812* (2013.01); *G01N 33/92* (2013.01); *G01N 2333/71* (2013.01); *G01N 2333/90* (2013.01); *G01N 2570/00* (2013.01); *G01N 2800/50* (2013.01); *G01N 2800/52* (2013.01); *Y10T 436/24* (2015.01)

(58) Field of Classification Search
CPC ........ A61B 5/00; A61B 5/41; G01N 2333/71; G01N 2333/90; G01N 2570/00; G01N 2800/50; G01N 2800/52; G01N 33/57415; G01N 33/57484; G01N 33/48; G01N 33/49; G01N 33/6812; G01N 33/92; Y10T 436/24
USPC ........... 436/63, 71, 86, 89, 161, 173; 435/29
See application file for complete search history.

(56) References Cited

U.S. PATENT DOCUMENTS

| | | | |
|---|---|---|---|
| 10,962,542 B2* | 3/2021 | Lopes Carvalho | ......................... G01N 33/57484 |
| 11,181,525 B2* | 11/2021 | Nagourney | ........ G01N 33/6812 |
| 2013/0023056 A1* | 1/2013 | Raftery | ............ G01N 33/57415 562/478 |
| 2013/0172430 A1* | 7/2013 | Lisanti | .................... G01N 30/00 73/61.52 |
| 2014/0162903 A1* | 6/2014 | Raftery | ............ G01N 33/57415 506/15 |

* cited by examiner

*Primary Examiner* — Maureen Wallenhorst
(74) *Attorney, Agent, or Firm* — Fitzsimmons IP Law

(57) ABSTRACT

The present invention relates to a metabolic biomarker set for use in assessing breast cancer in a mammalian subject. In particular, the invention relates to a metabolic biomarker set for screening and/or diagnosing breast cancer, the metabolic biomarker set including at least (a) one amino acid selected from glutamine, glutamate and serine, and one lipid, or (b) glutamine and glutamate. Further, the invention relates to a metabolic biomarker set for prediction of therapeutic response to breast cancer neoadjuvant chemotherapy. Moreover, the present invention relates to a method for assessing breast cancer, which includes obtaining a biological sample, preferably blood, from a mammalian subject and measuring in the biological sample the amount and/or ratios of metabolites. By employing the specific biomarkers and the method according to the present invention it becomes possible to more properly and reliably assess breast cancer.

20 Claims, 16 Drawing Sheets

Fig. 6A
Fig. 6B
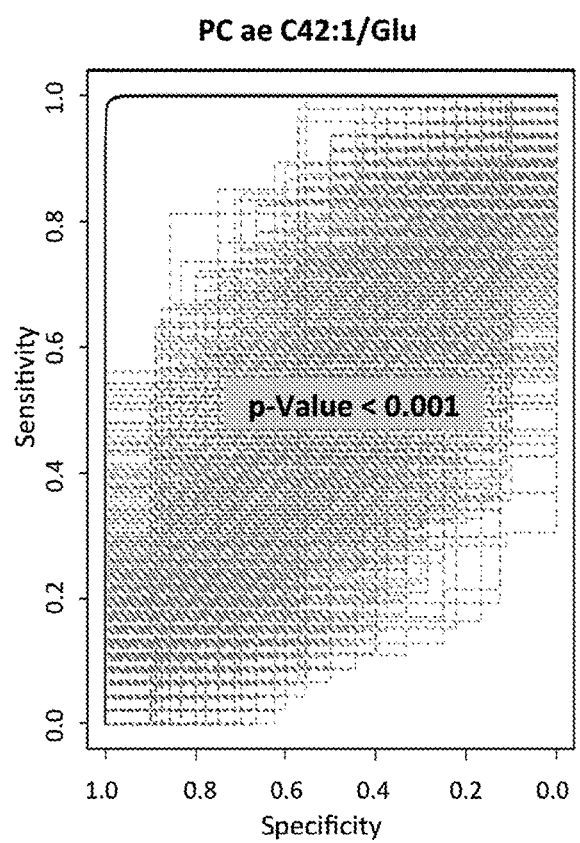
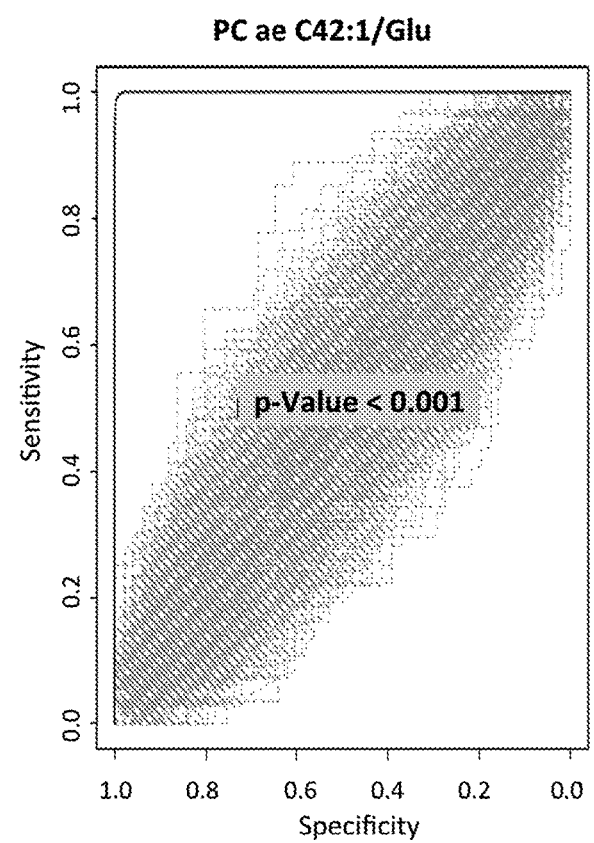

BIOMARKERS FOR ASSESSING BREAST CANCER

TECHNICAL FIELD

The present invention relates to new biomarkers for assessing breast cancer. In particular, the present invention provides new biomarkers for use in screening and/or diagnosing breast cancer in patients, prediction of therapeutic response to breast cancer neoadjuvant chemotherapy, assessing biochemical reflects of breast cancer tumor activity, and categorizing breast cancer tumors according to their intrinsic subtypes. Moreover, the present invention relates to a method for assessing breast cancer in a mammalian subject, and to a kit for carrying out the method. Moreover, the present invention relates to a method for assessing breast cancer, which comprises obtaining a biological sample, preferably blood, from a mammalian subject and measuring in the biological sample the amount and/or ratio of metabolites. By employing the specific biomarkers and the methods according to the present invention it becomes possible to more properly and reliably assess breast cancer.

BACKGROUND ART

Metabolomics

Metabolomics is a comprehensive quantitative measurement of low molecular weight compounds covering systematically the key metabolites, which represent the whole range of pathways of intermediary metabolism. The capability to analyze large arrays of metabolites extracts biochemical information reflecting true functional end-points of overt biological events while other functional genomics technologies such as transcriptomics and proteomics, though highly valuable, merely indicate the potential cause for phenotypic response. Therefore they cannot necessarily predict drug effects, toxicological response or disease states at the phenotype level unless functional validation is added.

Metabolomics bridges this information gap by depicting in particular such functional information since metabolite differences in biological fluids and tissues provide the closest link to the various phenotypic responses. Needless to say, such changes in the biochemical phenotype are of direct interest to pharmaceutical, biotech and health industries once appropriate technology allows the cost-efficient mining and integration of this information.

In general, phenotype is not necessarily predicted by genotype. The gap between genotype and phenotype is spanned by many biochemical reactions each with individual dependencies to various influences, including drugs, nutrition and environmental factors. In this chain of biomolecules from the genes to phenotype, metabolites are the quantifiable molecules with the closest link to phenotype. Many phenotypic and genotypic states, such as a toxic response to a drug or disease prevalence are predicted by differences in the concentrations of functionally relevant metabolites within biological fluids and tissue.

Breast Cancer

Breast cancer is a type of cancer originating from breast tissue, most commonly from the inner lining of milk ducts or the lobules that supply the ducts with milk. Worldwide, breast cancer accounts for 22.9% of all cancers (excluding non-melanoma skin cancers) in women. In 2012, about 226,870 females in the U.S. were diagnosed with breast cancer, which represents 29% of all newly diagnosed female cancer patients leading to more than 39,000 deaths in the U.S. in 2011, being ranked as the second leading cause of cancer death in women. Early diagnosis can significantly increase long-term survival rates for breast cancer and currently, mammography is the most acceptable and effective screening procedure for the detection of breast cancer and was recommended by the U.S. Preventive Services Task Force (USPSTF) to women over 40 years old. However, because of the high false positive rate of this screen, the USPSTF revised their recommendation to a reduced frequency of mammogram screening in 2009. Other imaging techniques, such as ultrasonography and magnetic resonance imaging, have also been used in breast cancer screening. Unfortunately, even with the inclusion of these imaging techniques, about 20% of breast cancer patients still cannot be detected.

New methods for screening and diagnosing would be very helpful especially in developing countries with continental dimensions where mammography specialized services are not offered to every woman over 40 years of age. Only in Brazil for example, around 30 million women per year are eligible to mammography exams, however, less than 50% will have access to this exam. The result is that, among the 52.000 new cases/year, more than 60% correspond to advanced cases that will need a pre-surgical chemotherapy to diminish the disproportionate large tumor volumes in order to make surgery possible.

Therefore, an urgent need exists in the art for new screening procedures, which can be easily performed, i.e. without the need of specialized equipment or resources. Further, there is an urgent need for the provision of more reliable and effective methods for diagnosing of breast cancer with high accuracy as well as for methods for prediction of disease progression and response to chemotherapy.

One promising approach for screening in diagnosing breast cancer is the use of biomarkers, such as plasma (or serum) biomarkers (such as antigens and protein patterns). However, they are still far from clinical use. Some tumor markers, such as CA15.3 and CA27.29, are recommended only for therapeutic monitoring, but not screening.

Therefore, new effective biomarkers for breast cancer screening and diagnosing that can be used individually or in combination with other existing methods are urgently needed.

Recently, it has been discovered that the metabolic properties of cancer cells are different from those of normal cells, as it is dependent on aerobic glycolysis, fatty acid synthesis and glutaminolysis for proliferation. Enhanced fatty acid synthesis, for example, provides rapidly proliferating tumor cells lipids for membrane biogenesis, conferring both a growth and survival advantage. Similarly, cancer cells are extremely sensitive to glutamine deprivation and cannot proliferate in culture without it. 'Glutamine addiction' results in enhanced production of byproducts necessary for rapidly proliferating cells, such as amino-acid precursors and as a result the dysregulated cellular metabolism is also linked to drug resistance in cancer therapy. Indeed, Fatty Acid Synthase (FASN), a key complex catalyzing fatty acid synthesis is linked to acquired Taxol/Trastuzumab/Adriamycin resistance in breast cancer or intrinsic gemcitabine and radiation resistance in pancreatic cancer. Finally, glutaminolysis is linked to cisplatin resistance via the activation of mammalian target of Rapamycin Complex 1 (mTORC1) signaling in gastric cancer.

Breast cancer is usually treated with surgery, which may be followed by chemotherapy or radiation therapy, or both. Neoadjuvant chemotherapy has mainly been used to help treating locally advanced breast cancers specially those ones considered inoperable at the first visit. In the last years however, it has been increasingly used for smaller and operable tumors in order to spare and preserve larger portions of breast tissue than would, otherwise, be removed at primary surgery. Another peculiarity of this treatment approach is that it provides a unique opportunity to accurately quantitate, by clinical and/or radiological exams, the tumor volume variations in response to the adopted chemotherapy regimen.

Moreover, type of therapy, selection of drugs and dosage regimen has conventionally been set by merely determining the tumor's size. Tumor size, however, does not reflect its biochemical and metabolic activity, and therefore does likewise not reflect whether the tumor may be highly aggressive or inactive. Thus, the tools conventionally used in the art have been insufficient to properly define treatment of breast cancer in the patient.

The valuable information with regard to a breast cancer tumor's metabolomic activity is used in the invention not only to indicate alternative regimens when minimal or no response to chemotherapy is observed but also identify the patients achieving complete pathologic response (pCR) and, therefore, with more favorable outcomes.

Major efforts in the art have been directed to the development of predictive tools able to collaborate in the identification of patients that have higher chances to reach pCR as ypT0/ypN0. In addition, the occurrence of disease progression is also a major concern with the use of neoadjuvant chemotherapy and while many researchers have sought to determine clinical and molecular predictors of a pCR very few have reported on predictors of progression.

Wei, S., et al. (Metabolomics approach for predicting response to neoadjuvant chemotherapy for breast cancer, Molecular Oncology (2012)) developed a prediction model by combining NMR and MS derived metabolites, which correctly identified 80% of the patients whose tumors did not show complete response to chemotherapy. A combination of four metabolites, three detected by NMR (threonine glutamine and isoleucine), and one by MS (linolenic acid) could distinguish groups of patients with no, partial or complete response. However, the number of correctly identified patients of 80% is still not satisfactory.

Qiu, Y. et al. (Mass Spectrometry-Based Quantitative Metabolomics Revealed a Distinct Lipid Profile in Breast Cancer Patients, Int. J. Mol. Sci. 2013) developed a diagnostic equation based on three metabolites (lysoPC a C16:0, PC ae C42:5 and PC aa C34:2) which successfully differentiated breast cancer patients from healthy controls, with a sensitivity of 98.1% and a specificity of 96.0%. However, the authors were not able to generate predictive results for chemotherapy response as well as any result capable of categorizing breast cancer tumors according to their intrinsic subtypes. Consequently, there still remains room, not only for sensitivity and specificity improvements, but also for a significant expansion in the applicability of the model.

Therefore, there is an urgent need in the art to develop new screening and diagnosing techniques suitable for identifying breast cancer in patients with high accuracy and reliability, identifying the tumor subtype and its status of activity, predicting breast cancer progression, outcome of the disease as well as the patient's therapeutic response to chemotherapy.

Technical Problem

Based on these cancer specific metabolic changes, the inventors have aimed to identify new blood metabolite signatures, i.e. new biomarkers that could help in the population screening of breast cancer as well as for diagnosing breast cancer in a subject. Further, it has been aimed to identify blood metabolite signatures for predicting disease progression as well as predicting the patient's therapeutic response to chemotherapy.

In view of the above-mentioned problems existing in the art, the object underlying the present invention is the provision of new biomarkers for assessing breast cancer, which markers allow for screening and diagnosis of breast cancer already in an early stage of disease progression and with high accuracy and reliability. Optimally, the marker should be easily detectable in a biological sample such as in blood and its level should be consistently related to the stage of breast cancer. Moreover, it is an object of the present invention to provide for a method for assessing breast cancer in a biological sample, which allows for fast, convenient and high throughput performance. Furthermore, the new biomarkers should be suitable for predicting breast cancer progression, outcome of the disease as well as the patient's therapeutic response to chemotherapy.

In order to solve the objects underlying the present invention the inventors based their investigations on metabolomics as it could give insight in the biochemical changes occurring in the course of breast cancer development and offer several novel and potentially better biomarkers. The inventors found that a more comprehensive picture of all metabolomics pathways and mechanisms involved in breast cancer is given when using a panel of metabolites that are altered with progressing breast cancer rather than employing the screening techniques performed in the art, such as mammography or other imaging techniques.

SUMMARY OF THE INVENTION

Therefore, the present invention, as defined in the claims attached, provides for new biomarkers (i.e. a new biomarker set) suitable for assessing breast cancer, particularly at an early stage of disease. Moreover, the present invention also provides for a method for assessing breast cancer in a mammalian subject on the basis of the biomarkers and biomarker sets as described herein, as well as a kit adapted to carry out the method.

BRIEF DESCRIPTION OF THE FIGURES

In the specification reference is made to FIGS. 1-15, which demonstrate examples according to the invention of the increase or decrease of a metabolic biomarker in progressing breast cancer.

FIG. 6A: ROC curve analysis obtained during the Training Set using two metabolites Glutamate (Glu) and Phosphatidylcholine Acyl-Alkyl C42:1 (PC ae C42:1).

FIG. 6B: ROC curve analysis obtained during the Validation Set using two metabolites Glutamate (Glu) and Phosphatidylcholine Acyl-Alkyl C42:1 (PC ae C42:1).

DESCRIPTION OF THE PREFERRED EMBODIMENTS

Figure 1A:
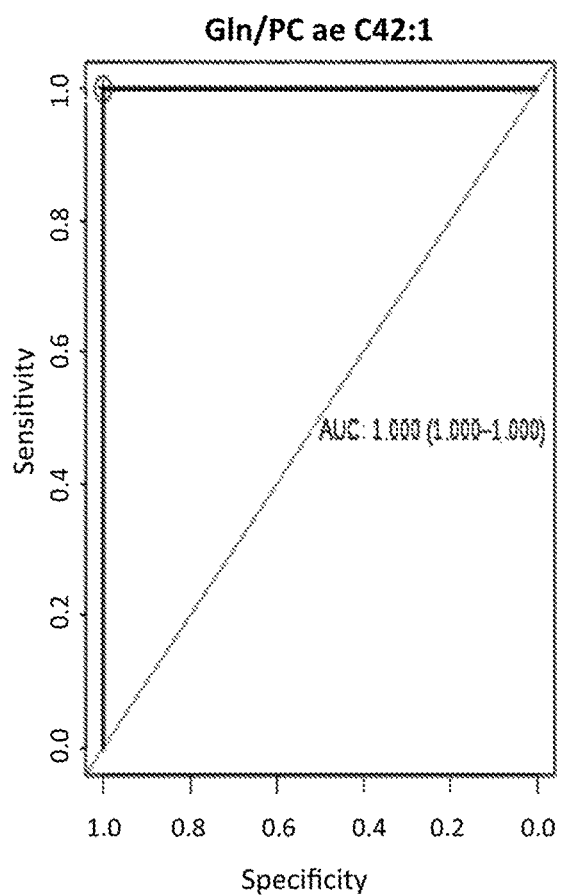
FIG. 1A: ROC curve analysis obtained during the Training Set using two metabolites Glutamine (Gln) and Phosphatidylcholine Acyl-Alkyl C42:1 (PC ae C42:1).

By employing the specific (sets of) biomarkers and the methods according to the present invention it has become possible to assess breast cancer with improved accuracy and reliability.

"Assessing" in the sense of the present invention means screening of subjects potentially suffering from breast cancer, the diagnosis of breast cancer in subjects and monitoring the progression of the disease, in particular the detection and marking of the disease at the different stages and/or sub-classification of the tumor(s). Further, "assessing" encompasses the prediction of whether a patient suffering from breast cancer is likely to respond to chemotherapy, particularly to neoadjuvant chemotherapy. Furthermore, "assessing" relates to the determination and characterization of biochemical reflection of breast cancer tumor activity. Furthermore "assessing" in the sense of the present invention means the possibility to positively identify a breast cancer tumor subtype in a patient and to discriminate between certain breast cancer tumors according to their intrinsic subtypes.

It has surprisingly been achieved in the present invention to provide biomarkers or biomarker sets by measuring the amount and/or ratios of certain metabolies in samples, such as blood samples, of subjects that make it possible to screen and diagnose breast cancer in an improved manner and at an early stage of the disease and allow for a more accurate and reliable prediction of whether a patient suffering from breast cancer will likely respond to chemotherapy, such as to neoadjuvant chemotherapy. In particular, the biomarkers and biomarker sets of the present invention make it possible to predict wether a patient is likely to reach complete pathological response (pCR) to chemotherapy or stable disease and/or progression (SDPR). Further, it has surprisingly been found in the present invention that subtypes of breast cancer tumors can be distinguished on the basis of their specific metabolite profile.

In the context of the present invention complete pathological response (pCR) is defined as no invasive or noninvasive residual in breast or nodes (ypTO ypNO), which means complete disappearance of tumor, after finishing chemotherapy, without any residual signal of cancer left in breast and lymph nodes. pCR is a suitable surrogate end point, particularly for patients harboring luminal B/HER2-negative, HER2-positive or triple negative disease. Thus, the present invention makes it possible to identify patients that have higher chances to reach pCR as ypTO ypNO.

In the context of the present invention stable disease and/or progression (SDPR) is defined according to the United States National Cancer Institute at the National Institute of Health. Thus, the terms "Stable Disease" and "Progression" denote, respectively, to a cancer that is neither decreasing nor increasing in extent or severity or denote to a cancer as it becomes worse or spreads in the body. Both situations are not desired specially after facing months of highly toxic chemotherapy regimens; hence both possibilities were combined in only one group (SDPR) in order to predict these unfavorable results.

In fact, the biomarkers according to the invention are easily detectable in biological samples, in particular in blood, and their level is consistently related to the degree of breast cancer.

In general, a biomarker is a valuable tool due to the possibility to distinguish two or more biological states from one another, working as an indicator of a normal biological process, a pathogenic process or as a reaction to a pharmaceutical intervention. A metabolite is a low molecular compound (<1 kDa), smaller than most proteins, DNA and other macromolecules. Small changes in activity of proteins result in big changes in the biochemical reactions and their metabolites (=metabolic biomarker, looking at the body's metabolism), whose concentrations, fluxes and transport mechanisms are sensitive to diseases and drug intervention. This enables getting an individual profile of physiological and pathophysiological substances, reflectling both genetics and environmental factors like nutrition, physical activity, gut microbal and medication. Thus, a metabolic biomarker gives more comprehensive information than for example a protein or hormone, which are biomarkers, but not metabolic biomarkers.

In view thereof, the term "metabolic biomarker" or short "biomarker" as used herein is defined to be a compound suitable as an indicator of the presence and state of breast cancer as well as of subtype of tumor, being a metabolite or metabolic compound occurring during metabolic processes in the mammalian body. The terms "biomarker" and "metabolic biomarker" are in general used synonymously in the context of the present invention and typically refer to the amount of a metabolite or to the ratio of two or more metabolites. Hence, the term metabolic biomarker or biomarker is intended to also comprise ratios between two or more metabolites.

The term "amount" typically refers to the concentration of a metabolite in a sample, such as blood sample, and is usually given in mol/l, but may also be measured in other units typically used in the art, such as g/l, mg/l or else. The term "sum" typically means the sum of amount of all metabolites as specified in the respective embodiment. The term "ratio" typically means the ratio of amounts of metabolites as specified in the respective embodiment.

The metabolic biomarker (set) measured according to the present invention may comprise the classes of metabolites (i.e. analytes) of amino acids and biogenic amines, acylcarnitines, hexoses, sphingolipids and glycerophospholipids, as listed in Tables 1 to 5 herein below. The definitions of these classes are known to the skilled person, however, preferred members of these classes are summarized in Tables 1 to 5 hereinbelow. Moreover, biogenic amines of Table 1 hereinbelow are understood as a group of naturally occurring biologically active compounds derived by enzymatic decarboxylation of the natural amino acids. A biogenic substance is a substance provided by life processes, and the biogenic amines contain an amine group.

Preferably, the metabolic biomarker (set) measured according to the present invention comprises the combination of biomarkers as specified in the claims.

It has surprisingly been found that measuring a set of biomarkers comprising these classes of metabolites, i.e. measuring the amount and/or ratios of certain indicative metabolites, allows for screening and/or diagnosing breast cancer in an improved manner and at an early stage of the disease, allows for the prediction of therapeutic response to breast cancer neoadjuvant chemotherapy, allows for assessing biochemical reflection of breast cancer tumor activity, and allows for subclassification between intrinsic breast cancer tumor subtypes.

If one metabolite or one class of metabolites as specified for the respective biomarker combination is omitted or if the number thereof is decreased the assessment of breast cancer becomes less sensitive and less reliable. This particularly applies for the early stages of the disease being not reliably detectable according to known methods using known biomarkers at all. In fact, the measurement of the metabolites contained in the respective sets of biomarkers at the same time allows a more accurate and more reliable assessment of breast cancer, typically with a sensitivity of preferably more than 80%, more preferably more than 90%, further more preferably more than 98% and most preferably 100%. Such a fact has neither been described in nor made obvious from the prior art.

Moreover, the biomarkers and biomarker sets of the present invention as described herein allow for a more reliable and accurate assessment of breast cancer with a specificity of more than 80%, more preferably more than 85%, further more preferably more than 90% and most preferably 100%.

Moreover, the biomarker set of the present invention as described herein allows for a more reliable assessment of breast cancer with a positive predictive value (PPV) of more than 40%, more preferably more than 50%, further more preferably more than 60% and most preferably more than 80%.

Moreover, the biomarker set of the present invention as described herein allows for a more reliable assessment of breast cancer with a negative predictive value (NPV) of more than 80%, more preferably more than 90%, further more preferably more than 98% and most preferably 100%.

In a preferred embodiment, the biomarker set of the present invention as described herein allows for a more reliable assessment of breast cancer with a sensitivity of 100% and a NPV of 100%.

The meaning of the terms "sensitivity", "specificity", "positive predictive value" and "negative predictive value" is typically known in the art and are defined in the context of the present invention according to the "Predictive Value Theory", established by the University of Iowa, USA.

In this theory, the diagnostic value of a procedure is defined by its sensitivity, specificity, predictive value and efficiency. The formulae are summarized below.

Sensitivity of a test is the percentage of all patients with disease present who have a positive test. TP=Test Positive; FN=False Negative $$(TP/(TP+FN)) \times 100 = \text{Sensitivity (\%)}$$

Specificity of a test is the percentage of all patients without disease who have a negative test. TN=Test Negative; FP=False Positive $$(TN/(FP+TN)) \times 100 = \text{Specificity (\%)}$$

The predictive value of a test is a measure (%) of the times that the value (positive or negative) is the true value, i.e. the percent of all positive tests that are true positives is the Positive Predictive Value.

$$(TP/(TP+FP)) \times 100 = \text{Predictive Value of a Positive Result (\%)}$$

$$(TN/(FN+TN)) \times 100 = \text{Predictive Value Negative Result (\%)}$$

The performance of biomarkers can further be assessed by determining the Positive and Negative Likelihood Ratios (LR) used herein during Statistical Univariate Analysis.

| LR | Interpretation |
|---|---|
| >10 | Large and often conclusive increase in the likelihood of disease |
| 5-10 | Moderate increase in the likelihood of disease |
| 2-5 | Small increase in the likelihood of disease |
| 1-2 | Minimal increase in the likelihood of disease |
| 1 | No change in the likelihood of disease |
| 0.5-1.0 | Minimal decrease in the likelihood of disease |
| 0.2-0.5 | Small decrease in the likelihood of disease |
| 0.1-0.2 | Moderate decrease in the likelihood of disease |
| <0.1 | Large and often conclusive decrease in the likelihood of disease |

In a more preferred embodiment, the biomarker set of the present invention as described herein allows for a more reliable assessment of breast cancer with a sensitivity of 100%, a specificity of 85% or more and a NPV of 100%.

In a more preferred embodiment, the biomarker set of the present invention as described herein allows for a more reliable assessment of breast cancer with a sensitivity of 100%, a specificity of 90% or more, a PPV of 80% or more, and a NPV of 100%.

In the most preferred embodiment, the biomarker set of the present invention as described herein allows for a more reliable assessment of breast cancer with a sensitivity of 100%, a specificity of 100%, a PPV of 100%, and a NPV of 100%.

As mentioned above, the disease to be assessed is breast cancer. Preferably it is breast cancer in stages I, II, III or IV, more preferably breast cancer in stage III, such as stage III a, b or c. Definition of the medical stages of breast cancer is defined by the American Joint Committee on Cancer (AJCC) of the United States National Cancer Institute at the National Institutes of Health (cf. Breast. In: Edge S B, Byrd D R, Compton C C, et al., eds.: AJCC Cancer Staging Manual. 7th ed. New York, N.Y.: Springer, 2010, pp 347-76). The staging system provides a strategy for grouping patients with respect to prognosis. Therapeutic decisions are formulated in part according to staging categories but primarily according to tumor size, lymph node status, estrogen-receptor and progesterone-receptor levels in the tumor tissue, human epidermal growth factor receptor 2 (HER2/neu) status, menopausal status, and the general health of the patient.

The biological sample is obtained from a mammal, preferably from a mouse, a rat, a guinea pig, a dog, a mini-pig, or a human, most preferably human, further preferably from a woman. The biological sample preferably is blood, however, any other biological sample known to the skilled person, which allows the measurements according to the present invention is also suitable. The blood sample typically is full blood, serum or plasma, wherein blood plasma is preferred. Dried samples collected in paper filter are also accepted. Thus, the methods according to the invention typically are in vitro methods.

For the measurement of the metabolite concentrations in the biological sample a quantitative analytical method such as chromatography, spectroscopy, and mass spectrometry is employed, while mass spectrometry is particularly preferred. The chromatography may comprise GC, LC, HPLC, and UHPLC; spectroscopy may comprise UV/Vis, IR, and NMR; and mass analyzers/spectrometry may comprise ESI-QqQ, ESI-QqTOF, MALDI-QqQ, MALDI-QqTOF, and MALDI-TOF-TOF. More preferably, mass analyzers/spectrometry comprises Quadrupole Mass Analyzers, Ion Trap Mass Analyzers, TOF (Time of Flight) Mass Analyzer, Orbitrap mass analyser, Magnetic Sector Mass Analyzer, Electrostatic Sector Mass Analyzer, Ion Cyclotron Resonance (ICR) and combinations of mass analyzers, including single quadrupole (Q) and triple quadrupole (QqQ), QqTOF, TOF-TOF, Q-Orbitrap. Preferred is the use of FIA- and HPLC-tandem mass spectrometry.

Abbreviations are as follows: GC=Gas Chromatography, CE=Capillary electrophoresis, LC=Liquid Chromatography, HPLC=High Preasure Liquid Chromatography, UHPLC=Ultra High Preasure Liquid Chromatography, UV-Vis=Ultraviolet-Visible, IR=Infrared, NIR=Near Infrared, NMR=Nuclear Magnetic Ressonance, ESI=Electron Spray Ionization, MALDI=Matrix-assisted laser desorption/ionization, TOF=Time-of-Flight, APCI=Atmospheric pressure chemical ionization, QqQ=Triple quadrupole configuration also known as Q1q2Q3 (Q1 and Q3 quadrupoles are mass filters and q2 is a no mass-resolving quadrupole).

For measuring the metabolite amounts targeted metabolomics is used to quantify the metabolites in the biological sample including the analyte classes of amino acids, biogenic amines, acylcarnitines, hexoses, sphingolipids and glycerophospholipids. The quantification is done using in the presence of isotopically labeled internal standards and determined by the methods as described above. A list of analytes including their abbreviations (BC codes) being suitable as metabolites to be measured according to the invention is indicated in the following Tables.

TABLE 1

| Amino acids and biogenic amines (µM) | |
|---|---|
| BC code | Analyte |
| Ala | Alanine |
| Arg | Arginine |
| Asn | Asparagine |
| Asp | Aspartate |
| Cit | Citrulline |
| Gln | Glutamine |
| Glu | Glutamate |
| Gly | Glycine |
| His | Histidine |
| Ile | Isoleucine |
| Leu | Leucine |
| Lys | Lysine |
| Met | Methionine |
| Orn | Ornithine |
| Phe | Phenylalanine |
| Pro | Proline |
| Ser | Serine |
| Thr | Threonine |
| Trp | Tryptophane |
| Tyr | Tyrosine |
| Val | Valine |
| Ac-Orn | Acetylornithine |
| ADMA | Asymmetric dimethylarginine |
| SDMA | Symmetric dimethylarginine |
| total DMA | Total dimethylarginine |
| alpha-AAA | alpha-Aminoadipic acid |
| Carnosine | Carnosine |
| Creatinine | Creatinine |
| Histamine | Histamine |
| Kynurenine | Kynurenine |
| Met-SO | Methioninesulfoxide |
| Nitro-Tyr | Nitrotyrosine |
| OH-Pro | Hydroxyproline |
| PEA | Phenylethylamine |
| Putrescine | Putrescine |
| Sarcosine | Sarcosine |
| Serotonin | Serotonin |
| Spermidine | Spermidine |
| Spermine | Spermine |
| Taurine | Taurine |

TABLE 2

Acylcarnitine (μM)

| BC code | Analyte |
| --- | --- |
| C0 | Carnitine |
| C2 | Acetylcarnitine |
| C3 | Propionylcarnitine |
| C3:1 | Propenoylcarnitine |
| C3-OH | Hydroxypropionylcarnitine |
| C4 | Butyrylcarnitine |
| C4:1 | Butenylcarnitine |
| C4-OH (C3-DC) | Hydroxybutyrylcarnitine |
| C5 | Valerylcarnitine |
| C5:1 | Tiglylcarnitine |
| C5:1-DC | Glutaconylcarnitine |
| C5-DC (C6-OH) | Glutarylcarnitine* (Hydroxyhexanoylcarnitine) |
| C5-M-DC | Methylglutarylcarnitine |
| C5-OH (C3-DC-M) | Hydroxyvalerylcarnitine (Methylmalonylcarnitine) |
| C6 (C4:1-DC) | Hexanoylcarnitine (Fumarylcarnitine) |
| C6:1 | Hexenoylcarnitine |
| C7-DC | Pimelylcarnitine |
| C8 | Octanoylcarnitine |
| C9 | Nonaylcarnitine |
| C10 | Decanoylcarnitine |
| C10:1 | Decenoylcarnitine |
| C10:2 | Decadienylcarnitine |
| C12 | Dodecanoylcarnitine |
| C12:1 | Dodecenoylcarnitine |
| C12-DC | Dodecanedioylcarnitine |
| C14 | Tetradecanoylcarnitine |
| C14:1 | Tetradecenoylcarnitine |
| C14:1-OH | Hydroxytetradecenoylcarnitine |
| C14:2 | Tetradecadienylcarnitine |
| C14:2-OH | Hydroxytetradecadienylcarnitine |
| C16 | Hexadecanoylcarnitine |
| C16:1 | Hexadecenoylcarnitine |
| C16:1-OH | Hydroxyhexadecenoylcarnitine |
| C16:2 | Hexadecadienylcarnitine |
| C16:2-OH | Hydroxyhexadecadienylcarnitine |
| C16-OH | Hydroxyhexadecanoylcarnitine |
| C18 | Octadecanoylcarnitine |
| C18:1 | Octadecenoylcarnitine |
| C18:1-OH | Hydroxyoctadecenoylcarnitine |
| C18:2 | Octadecadienylcarnitine |
| C10:1 | Decenoylcarnitine |
| C10:2 | Decadienylcarnitine |
| C12 | Dodecanoylcarnitine |
| C12:1 | Dodecenoylcarnitine |
| C12-DC | Dodecanedioylcarnitine |
| C14 | Tetradecanoylcarnitine |
| C14:1 | Tetradecenoylcarnitine |
| C14:1-OH | Hydroxytetradecenoylcarnitine |
| C14:2 | Tetradecadienylcarnitine |
| C14:2-OH | Hydroxytetradecadienylcarnitine |
| C16 | Hexadecanoylcarnitine |

TABLE 3

Hexoses (mM)

| BC code | Analyte |
| --- | --- |
| H1 | Hexose |

TABLE 4

Sphingolipids (mM)

| BC code | Analyte |
| --- | --- |
| SM (OH) C14:1 | Hydroxysphingomyelin with acyl residue sum C14:1 |
| SM (OH) C16:1 | Hydroxysphingomyelin with acyl residue sum C16:1 |
| SM (OH) C22:1 | Hydroxysphingomyelin with acyl residue sum C22:1 |
| SM (OH) C22:2 | Hydroxysphingomyelin with acyl residue sum C22:2 |
| SM (OH) C24:1 | Hydroxysphingomyelin with acyl residue sum C24:1 |

TABLE 4-continued

Sphingolipids (mM)

| BC code | Analyte |
| --- | --- |
| SM C16:0 | Sphingomyelin with acyl residue sum C16:0 |
| SM C16:1 | Sphingomyelin with acyl residue sum C16:1 |
| SM C18:0 | Sphingomyelin with acyl residue sum C18:0 |
| SM C18:1 | Sphingomyelin with acyl residue sum C18:1 |
| SM C20:2 | Sphingomyelin with acyl residue sum C20:2 |
| SM C22:3 | Sphingomyelin with acyl residue sum C22:3 |
| SM C24:0 | Sphingomyelin with acyl residue sum C24:0 |
| SM C24:1 | Sphingomyelin with acyl residue sum C24:1 |
| SM C26:0 | Sphingomyelin with acyl residue sum C26:0 |
| SM C26:1 | Sphingomyelin with acyl residue sum C26:1 |

TABLE 5

Glycerophospholipids (mM)

| BC code | Analyte |
| --- | --- |
| lysoPC a C14:0 | Lysophosphatidylcholine with acyl residue C14:0 |
| lysoPC a C16:0 | Lysophosphatidylcholine with acyl residue C16:0 |
| lysoPC a C16:1 | Lysophosphatidylcholine with acyl residue C16:1 |
| lysoPC a C17:0 | Lysophosphatidylcholine with acyl residue C17:0 |
| lysoPC a C18:0 | Lysophosphatidylcholine with acyl residue C18:0 |
| lysoPC a C18:1 | Lysophosphatidylcholine with acyl residue C18:1 |
| lysoPC a C18:2 | Lysophosphatidylcholine with acyl residue C18:2 |
| lysoPC a C20:3 | Lysophosphatidylcholine with acyl residue C20:3 |
| lysoPC a C20:4 | Lysophosphatidylcholine with acyl residue C20:4 |
| lysoPC a C24:0 | Lysophosphatidylcholine with acyl residue C24:0 |
| lysoPC a C26:0 | Lysophosphatidylcholine with acyl residue C26:0 |
| lysoPC a C26:1 | Lysophosphatidylcholine with acyl residue C26:1 |
| lysoPC a C28:0 | Lysophosphatidylcholine with acyl residue C28:0 |
| lysoPC a C28:1 | Lysophosphatidylcholine with acyl residue C28:1 |
| PC aa C24:0 | Phosphatidylcholine with diacyl residue sum C24:0 |
| PC aa C26:0 | Phosphatidylcholine with diacyl residue sum C26:0 |
| PC aa C28:1 | Phosphatidylcholine with diacyl residue sum C28:1 |
| PC aa C30:0 | Phosphatidylcholine with diacyl residue sum C30:0 |
| PC aa C30:2 | Phosphatidylcholine with diacyl residue sum C30:2 |
| PC aa C32:0 | Phosphatidylcholine with diacyl residue sum C32:0 |
| PC aa C32:1 | Phosphatidylcholine with diacyl residue sum C32:1 |
| PC aa C32:2 | Phosphatidylcholine with diacyl residue sum C32:2 |
| PC aa C32:3 | Phosphatidylcholine with diacyl residue sum C32:3 |
| PC aa C34:1 | Phosphatidylcholine with diacyl residue sum C34:1 |
| PC aa C34:2 | Phosphatidylcholine with diacyl residue sum C34:2 |
| PC aa C34:3 | Phosphatidylcholine with diacyl residue sum C34:3 |
| PC aa C34:4 | Phosphatidylcholine with diacyl residue sum C34:4 |
| PC aa C36:0 | Phosphatidylcholine with diacyl residue sum C36:0 |
| PC aa C36:1 | Phosphatidylcholine with diacyl residue sum C36:1 |
| PC aa C36:2 | Phosphatidylcholine with diacyl residue sum C36:2 |
| PC aa C36:3 | Phosphatidylcholine with diacyl residue sum C36:3 |
| PC aa C36:4 | Phosphatidylcholine with diacyl residue sum C36:4 |
| PC aa C36:5 | Phosphatidylcholine with diacyl residue sum C36:5 |
| PC aa C36:6 | Phosphatidylcholine with diacyl residue sum C36:6 |
| PC aa C38:0 | Phosphatidylcholine with diacyl residue sum C38:0 |
| PC aa C38:1 | Phosphatidylcholine with diacyl residue sum C38:1 |
| PC aa C38:3 | Phosphatidylcholine with diacyl residue sum C38:3 |
| PC aa C38:4 | Phosphatidylcholine with diacyl residue sum C38:4 |
| PC aa C38:5 | Phosphatidylcholine with diacyl residue sum C38:5 |
| PC aa C38:6 | Phosphatidylcholine with diacyl residue sum C38:6 |
| PC aa C40:1 | Phosphatidylcholine with diacyl residue sum C40:1 |
| PC aa C40:2 | Phosphatidylcholine with diacyl residue sum C40:2 |
| PC aa C40:3 | Phosphatidylcholine with diacyl residue sum C40:3 |
| PC aa C40:4 | Phosphatidylcholine with diacyl residue sum C40:4 |
| PC aa C40:5 | Phosphatidylcholine with diacyl residue sum C40:5 |
| PC aa C40:6 | Phosphatidylcholine with diacyl residue sum C40:6 |
| PC aa C42:0 | Phosphatidylcholine with diacyl residue sum C42:0 |
| PC aa C42:1 | Phosphatidylcholine with diacyl residue sum C42:1 |
| PC aa C42:2 | Phosphatidylcholine with diacyl residue sum C42:2 |
| PC aa C42:4 | Phosphatidylcholine with diacyl residue sum C42:4 |
| PC aa C42:5 | Phosphatidylcholine with diacyl residue sum C42:5 |
| PC aa C42:6 | Phosphatidylcholine with diacyl residue sum C42:6 |
| PC ae C30:0 | Phosphatidylcholine with acyl-alkyl residue sum C30:0 |
| PC ae C30:1 | Phosphatidylcholine with acyl-alkyl residue sum C30:1 |
| PC ae C30:2 | Phosphatidylcholine with acyl-alkyl residue sum C30:2 |
| PC ae C32:1 | Phosphatidylcholine with acyl-alkyl residue sum C32:1 |

TABLE 5-continued

Glycerophospholipids (mM)

| BC code | Analyte |
|---|---|
| PC ae C32:2 | Phosphatidylcholine with acyl-alkyl residue sum C32:2 |
| PC ae C34:0 | Phosphatidylcholine with acyl-alkyl residue sum C34:0 |
| PC ae C34:1 | Phosphatidylcholine with acyl-alkyl residue sum C34:1 |
| PC ae C34:2 | Phosphatidylcholine with acyl-alkyl residue sum C34:2 |
| PC ae C34:3 | Phosphatidylcholine with acyl-alkyl residue sum C34:3 |
| PC ae C36:0 | Phosphatidylcholine with acyl-alkyl residue sum C36:0 |
| PC ae C36:1 | Phosphatidylcholine with acyl-alkyl residue sum C36:1 |
| PC ae C36:2 | Phosphatidylcholine with acyl-alkyl residue sum C36:2 |
| PC ae C36:3 | Phosphatidylcholine with acyl-alkyl residue sum C36:3 |
| PC ae C36:4 | Phosphatidylcholine with acyl-alkyl residue sum C36:4 |
| PC ae C36:5 | Phosphatidylcholine with acyl-alkyl residue sum C36:5 |
| PC ae C38:0 | Phosphatidylcholine with acyl-alkyl residue sum C38:0 |
| PC ae C38:1 | Phosphatidylcholine with acyl-alkyl residue sum C38:1 |
| PC ae C38:2 | Phosphatidylcholine with acyl-alkyl residue sum C38:2 |
| PC ae C38:3 | Phosphatidylcholine with acyl-alkyl residue sum C38:3 |
| PC ae C38:4 | Phosphatidylcholine with acyl-alkyl residue sum C38:4 |
| PC ae C38:5 | Phosphatidylcholine with acyl-alkyl residue sum C38:5 |
| PC ae C38:6 | Phosphatidylcholine with acyl-alkyl residue sum C38:6 |
| PC ae C40:1 | Phosphatidylcholine with acyl-alkyl residue sum C40:1 |
| PC ae C40:2 | Phosphatidylcholine with acyl-alkyl residue sum C40:2 |
| PC ae C40:3 | Phosphatidylcholine with acyl-alkyl residue sum C40:3 |
| PC ae C40:4 | Phosphatidylcholine with acyl-alkyl residue sum C40:4 |
| PC ae C40:5 | Phosphatidylcholine with acyl-alkyl residue sum C40:5 |
| PC ae C40:6 | Phosphatidylcholine with acyl-alkyl residue sum C40:6 |
| PC ae C42:0 | Phosphatidylcholine with acyl-alkyl residue sum C42:0 |
| PC ae C42:1 | Phosphatidylcholine with acyl-alkyl residue sum C42:1 |
| PC ae C42:2 | Phosphatidylcholine with acyl-alkyl residue sum C42:2 |
| PC ae C42:3 | Phosphatidylcholine with acyl-alkyl residue sum C42:3 |
| PC ae C42:4 | Phosphatidylcholine with acyl-alkyl residue sum C42:4 |
| PC ae C42:5 | Phosphatidylcholine with acyl-alkyl residue sum C42:5 |
| PC ae C44:3 | Phosphatidylcholine with acyl-alkyl residue sum C44:3 |
| PC ae C44:4 | Phosphatidylcholine with acyl-alkyl residue sum C44:4 |
| PC ae C44:5 | Phosphatidylcholine with acyl-alkyl residue sum C44:5 |
| PC ae C44:6 | Phosphatidylcholine with acyl-alkyl residue sum C44:6 |

Further preferred embodiments of the present invention are described in the following. However, their combination with features described further above is not intended to be excluded.

Screening and/or Diagnosis of Breast Cancer

In a first embodiment, the biomarkers and biomarker sets of the present invention are used for screening of subjects, such as human patients, potentially suffering from breast cancer and diagnosis of breast cancer in these subjects. It has surprisingly been found in the present invention that the biomarkers and biomarker sets as described herein are particularly useful for fast, easy and highthroughput screening of a large number of subjects, such as human patients, and for diagnosis of breast cancer from blood samples of these subjects with improved accuracy of results. Thus, in this embodiment assessing comprises screening and/or diagnosis of breast cancer in a mammalian subject, preferably in a human.

Thus, the invention is directed to the use of a combination of metabolites comprising at least
 (a) one amino acid selected from glutamine, glutamate and serine, and one lipid, or
 (b) glutamine and glutamate,
as a biomarker set for screening and/or diagnosing breast cancer.

The invention is further directed to a method for screening and/or diagnosis of breast cancer in a mammalian subject or a population of mammalian subjects, the method comprising measuring in a blood sample obtained from the subject the amount of at least
 (a) one amino acid selected from glutamine, glutamate and serine, and one lipid, or
 (b) glutamine and glutamate.

Although accuracy and reliability of screening and/or diagnosis, as determined by the parameters of one or more of specificity, sensitivity, PPV and NPV, by using the above-specified biomarker combination is already greatly improved compared with the prior art techniques, such as mammography, the accuracy and reliability can be further improved by using one or more, preferably two or more, further preferably three or more additional metabolites.

Hence, in a preferred embodiment the biomarker set further comprises one or more additional amino acid, such as those included in Table 1. The additional amino acids are preferably selected from glucogenic/ketogenic amino acids such as glycine, cysteine, alanine, arginine, proline, aspartate, asparagine, methionine, isoleucine, leucine, lysine, threonine phenylalanine, tyrosine and tryptophan, most preferably asparagine and aspartate.

Moreover, the lipid is preferably selected from sphingolipids and glycerolipids, such as glycerophospholipids, e.g. one or more of the lipids included in Tables 4 and 5. Further preferably, the lipid is derived from arachidonic acid, preferably arachidonic acid derived lipids containing 38 or more carbon atoms, and most preferably is selected from arachidonic polyunsaturated phosphatidylcholine acyl-alkyl, arachidonic mono-unsaturated phosphatidylcholine acyl-alkyl and arachidonic saturated phosphatidylcholine acyl-alkyl.

In a further preferred embodiment, the combination of metabolites further comprises one or more of a sphingomyelin and glutaconyl carnitine.

Further, the method for screening and/or diagnosis of breast cancer preferably additionally comprises measuring the amount, or ratio of amounts, of one or more, preferably two ore more, further preferably three or more of the following:
 sum of arachidonic polyunsaturated phosphatidylcholines acyl-alkyl,
 sum of arachidonic mono-unsaturated phosphatidylcholines acyl-alkyl,
 sum of arachidonic saturated phosphatidylcholines acyl-alkyl,
 ratio of sum of arachidonic polyunsaturated phosphatidylcholines acyl-alkyl/sum of arachidonic mono-unsaturated phosphatidylcholines acyl-alkyl,
 ratio of sum of arachidonic mono-unsaturated phosphatidylcholines acyl-alkyl/sum of arachidonic saturated phosphatidylcholines acyl-alkyl,
 phosphatidylcholine acyl-alkyl C38:1,
 phosphatidylcholine acyl-acyl C28:1,
 sphingomyelin C24:1 and/or sphingomyelin C18:0, and
 glutaconylcarnitine.

Optionally, the method comprises the further step of identifying, on the basis of the amounts of metabolites and ratios of metabolites measured, those subjects suffering from breast cancer and further preferably treating breast cancer in these subjects, for example by chemotherapy.

As the method of this embodiment can be performed from blood samples, the method greatly increases the subject's compliance compared to prior art screening techniques, such as mammography. In particular, the method greatly increases reliability and sensitivity of the screening results, in particular reduces the number of false positive and false negative results, and is less time consuming, and thus can be performed with a high number of patients.

Further, the method greatly increases the subject's compliance compared to prior art screening techniques, such as mammography. In particular, the method greatly increases reliability and sensitivity of the screening results, in particular reduces the number of false positive and false negative results, and is less time consuming.

Prediction of Therapeutic Response to Neoadjuvant Chemotherapy

In another embodiment, the biomarkers and biomarker sets of the present invention are used for predicting whether a patient suffering from breast cancer is likely to respond to neoadjuvant chemotherapy. Neoadjuvant therapy is a modality of treatment given as a first step to reduce a tumor before the main treatment, which is usually surgery. Examples of neoadjuvant therapy include chemotherapy (such as cyclophosphamide, taxol, doxorubicin) radiation therapy, and hormone therapy (Tamoxifen, Aromatase Inhibitors).

Thus, the invention is further directed to the use of a combination of metabolites comprising the biomarker sets described in the following for predicting whether a mammalian subject suffering from breast cancer is likely to respond to neoadjuvant chemotherapy.

In particular, the invention is directed to the use of a combination of metabolites contained in a blood sample of a mammalian subject, the combination of metabolites comprising at least one amino acid selected from serine and glutamine,
methylated arginine,
one acylcarnitine and
one lipid as a biomarker set for prediction of therapeutic response to breast cancer neoadjuvant chemotherapy.

The invention is further directed to a method for prediction of therapeutic response to breast cancer neoadjuvant chemotherapy in a mammalian subject, the method comprising measuring in a blood sample obtained from the subject the amount of at least one amino acid selected from serine and glutamine,
methylated arginine,
one acyl carnitine, and
one lipid.

Although accuracy and reliability of the prediction, as determined by the parameters of one or more of specificity, sensitivity, PPV and NPV, by using the above-specified biomarker combination is already greatly improved compared with the prior art techniques, the accuracy and reliability can be further improved by using one or more, preferably two or more, further preferably three or more additional metabolites.

Preferably, methylated arginine is dimethylated arginine (DMA).

In a preferred embodiment the biomarker set further comprises one or more additional amino acid, such as those included in Table 1. The additional amino acids are preferably selected from glucogenic/ketogenic amino acids such as glycine, cysteine, alanine, arginine, proline, aspartate, asparagine, methionine, isoleucine, leucine, lysine, threonine phenylalanine, tyrosine and tryptophan, most preferably alanine, aspartate, asparagine, glutamate and glycine.

In a preferred embodiment the acyl carnitine is selected from those included in Table 2, further preferably is selected from one or more of glutaryl carnitine (C5-DC) and methylglutaryl carnitine (C5-M-DC) and dodecanedioylcarnitine (C12-DC). Further preferably, the combination of metabolites further comprises one ore more additional acyl carnitine, such as those that make it possible to calculate the beta and omega oxidation of fatty acids included in Table 2.

Moreover, the lipid is preferably selected from sphingolipids and glycerolipids, such as glycerophospholipids, e.g. one or more of lipids included in Tables 4 and 5. Further preferably, the arachidonic lipids (fatty acids containing 38 carbon atoms or more in the molecule) are selected from polyunsaturated lipids containing 4, 5 and 6 unsaturations, monounsaturated and saturated lipids.

Further preferably, the lipid is selected from phosphatidylcholine acyl-alkyl C44:6, phosphatidylcholine acyl-alkyl C44:5, phosphatidylcholine acyl-acyl C38:4, phosphatidylcholine acyl-alkyl C30:0, phosphatidylcholine acyl-alkyl C32:2, phosphatidylcholine acyl-alkyl C30:0, phosphatidylcholine acyl-alkyl C42:0, lysophosphatidylcholine a C17:0, lysophosphatidylcholine a C26:0, lysophosphatidylcholine a C30:0 and lysophosphatidylcholine a C24:0.

Further preferably, the combination of metabolites further comprises one or more of putrescine, spermine and dimethylated arginine.

The method for prediction of therapeutic response to breast cancer neoadjuvant chemotherapy preferably additionally comprises measuring the amount, or ratio of amounts, of one or more, preferably two ore more, further preferably three or more of: phosphatidylcholine acyl-alkyl C44:6, phosphatidylcholine acyl-alkyl C44:5, phosphatidylcholine acyl-acyl C38:4, phosphatidylcholine acyl-alkyl C30:0, phosphatidylcholine acyl-alkyl C32:2, phosphatidylcholine acyl-alkyl C30:0, phosphatidylcholine acyl-alkyl C42:0, lysophosphatidylcholine a C17:0, lysophosphatidylcholine a C26:0, lysophosphatidylcholine a C30:0, lysophosphatidylcholine a C24:0, putrescine, spermine, total of dimethylated arginine.

In a particularly preferred embodiment, the above described biomarker combinations can be used as a biomarker set for predicting a complete therapeutic response of a subject suffering from breast cancer to chemotherapy (high predictive value for pCR). Hence, in an alternative embodiment, the invention is directed to the use of a combination of metabolites as described above as a biomarker set for predicting complete therapeutic response of a subject suffering from breast cancer to chemotherapy (high predictive value for pCR).

Assessment of Biochemical Reflects of Breast Cancer Tumor Activity

In another embodiment, the present invention is directed to the use of a combination of metabolites contained in a blood sample of a mammalian subject, the combination of metabolites comprising at least one amino acid selected from glutamate, glutamine, alanine, glycine, serine and aspartate, and
one lipid as a biomarker set for assessing the biochemical reflects of breast cancer tumor activity.

The invention is further directed to a method for assessing biochemical reflects of breast cancer tumor activity in a mammalian subject, the method comprising measuring in a blood sample obtained from the subject the amount of at least one amino acid selected from glutamate, glutamine, alanine, glycine, serine and aspartate, and
one lipid.

It has surprisingly been discovered in the present invention that breast cancer tumor activity can be characterised by the measurement of certain metabolic biomarkers, which reflect the enzymatic activity of the tumor's metabolism. In the context of the present invention, the biochemical reflections (reflects or mirrors) of breast cancer activity are thus defined as the measurements of the precursor-to-product metabolites ratios that reflect enzymatic activity of important metabolism reactions related to carcinogenesis such as glutaminolysis, glycolysis, glutaminase activity, and alkylglycerone phosphate synthase activity (AGPS).

In particular, it has surprisingly been discovered that characterisiation of tumor activity by way of metabolic biomarkers is advantageous and superior compared to tumor characterisation as performed in the art, such as by measuring the size or volume of a tumor. In particular, it has been found that metabolic activity is generally independent from tumor size and thus provides a more suitable parameter for determining breast cancer activity. For example, type of therapy and dosage of drug, for example dosage during chemotherapy, has often been determined in the art by simply measuring the size of a tumor. However, the size of a tumor does not reflect the tumor's metabolomic activity, but tumors of the same size may be highly aggressive or even be inactive. Consequently, the patients are in need of adjusting therapy and treatment on the basis of the tumor's actual metabolic activity. Hence, the therapy applied in the art was often not sufficient or not suitable to affectively treat breast cancer in the patient. Assessing the biochemical or metabolic reflects of breast cancer tumor activity thus provides a suitable tool for adapting and adjusting the patient's therapy, thereby greatly increasing the patient's compliance and life quality.

The lipid is preferably selected from sphingolipids and glycerolipids, such as glycerophospholipids, e.g. one or more of the lipids included in Tables 4 and 5. Further preferably, the arachidonic lipids (fatty acids containing 38 carbons or more), are selected from polyunsaturated lipids containing 4, 5 and 6 unsaturations, monounsaturated and saturated lipids.

More preferably, the lipid is selected from phosphatidylcholine acyl-alkyl and phosphatidylcholine acyl-acyl.

Further preferably, the combination of metabolites further comprises one or more of leucine and ornithine.

The method for assessing biochemical reflection of breast cancer tumor activity preferably additionally comprises measuring the amount of, or ratio of amounts of, one or more, preferably two or more, more preferably three or more of leucine, ornithine, ratio from total phosphatidylcholine acyl-alkyl/total phosphatidylcholine (acyl-alkyl and acyl-acyl).

Subclassification of Breast Cancer Tumors

In another embodiment, the present invention is directed to the use of biomarkers and biomarker sets as described herein for subclassification of a breast cancer tumor in a mammalian subject.

Breast cancer classification and subclassification is typically performed on the basis of cell receptor status. Breast cancer cells may or may not have many different types of receptors, the three most important in the present classification being: estrogen receptor (ER), progesterone receptor (PR), and HER2. Cells with or without these receptors are called ER positive (ER+), ER negative (ER−), PR positive (PR+), PR negative (PR−), HER2 positive (HER2+), and HER2 negative (HER2-). Cells with none of these receptors are called basal-like or triple negative.

It has surprisingly been found in the present invention that blood metabolite signatures are specific for subtypes of tumors. Therefore, the biomarkers and biomarker sets as described herein are particularly useful for subclassification of breast cancer tumors in blood samples. Moreover, it is possible with the biomarkers and biomarker sets of the present invention to subdivide cancer-intrinsic subtypes into low responsive tumors and highly responsive tumors based on specific blood metabolite characteristics.

In particular, the invention provides a suitable tool for discrimination between the tumor subtypes of:

a) luminal A/luminal B type tumors being ER positive and/or PR positive (luminal A and B, ER+/PR+, ER+/PR−, ER−/PR+) but HER2-negative
b) luminal B-HER2-positive type tumors being ER and/or PR positive but also HER2 positive tumors (luminal B HER2+)
c) HER2-positive type tumors being ER negative and PR negative but HER2-positive
d) Triple negative type tumors (ER−, PR−, HER2-).

Therefore, it is possible with the present invention to positively identify and to discriminate between the above-mentioned types of breast cancer tumors in the blood.

Thus, the invention is further directed to use of a combination of metabolites contained in a blood sample of a mammalian subject, the combination of metabolites comprising at least
  one acylcarnitine containing at least 10 carbon atoms in the molecule, and
  one lipid containing a maximum of 3 unsaturations in the molecule as a biomarker set for subclassification between intrinsic breast cancer tumor subtypes.

The term "unsaturations" means the number of carbon-to-carbon double bonds contained in the lipid molecule.

The invention further provides a method for subclassification between intrinsic breast cancer tumor subtypes in a mammalian subject, the method comprising measuring in a blood sample obtained from the subject the amount of at least
  one acylcarnitine containing at least 10 carbon atoms in the molecule, and
  one lipid containing a maximum of 3 unsaturations in the molecule.

Further optional metabolites are selected from one or more of methionine sulfoxide, lysine, histidine, lysoPC a C24:0, lysoPC a C20:3, citruline and arginine.

The acyl carnitine is preferably selected from those included in Table 2, which contain more than 10 carbon atoms, preferably more than 12, further preferably more than 13 carbon atoms in the molecule, and further preferably is selected from one or more of glutaryl carnitine (C5-DC) and methylglutaryl carnitine (C5-M-DC) and dodecanedioylcarnitine (C12-DC).

The lipid is preferably selected from sphingolipids and glycerolipids, such as glycerophospholipids, e.g. one or more of the lipids included in Tables 4 and 5. Further preferably, the lipid is derived from arachidonic acid, most preferably those lipids having 38 or more carbon atoms in the molecule.

More preferably, the lipid is selected from phosphatidylcholine acyl-alkyl and phosphatidylcholine acyl-acyl, most preferably is selected from phosphatidylcholine acyl-acyl C38:3, phosphatidylcholine acyl-acyl C36:0, phosphatidylcholine acyl-acyl C42:0, phosphatidylcholine acyl-acyl C38:0, phosphatidylcholine acyl-alkyl C38: 1, phosphatidylcholine acyl-acyl C38:2 and phosphatidylcholine acyl-alkyl C40:1.

In a further preferred embodiment, the combination of metabolites further comprises one or more amino acids, preferably one or more amino acids selected from those included in Table 1, most preferably selected from one or more of arginine, methionine, butenyl carnitine, kynunerine and triptophane.

Moreover, comparisons of tumors with high versus low response, within the same subtype of tumor, show that the presence of a subtype of tumor is significantly associated with a particular blood metabolite signature.

In particular, it has surprisingly been found in the present invention that it is possible to discriminate between certain types of breast cancer tumors on the basis of biomarkers, which are specific for this tumor. Thus, in this preferred embodiment assessing comprises subclassification of breast cancer tumors in a mammalian subject, preferably in a human.

In a particularly preferred embodiment, the present invention is directed to a method for identifying a Luminal A-like tumor in a mammalian subject, which comprises measuring in the blood sample obtained from the subject the amount of at least one acylcarnitine containing at least 10 carbon atoms in the molecule, one PC aa containing a maximum of 3 unsaturations, and at least one amino acid.

In another preferred embodiment, the present invention is directed to a method for identifying a Luminal B-like HER2 negative tumor in a mammalian subject, which comprises measuring in the blood sample obtained from the subject the amount of at least one acyl carnitine containing at least 10 carbon atoms in the molecule, at least one PC aa containing a maximum of 3 unsaturations, at least one PC ae, at least one amino acid, and at least one lyso PC a.

In another preferred embodiment, the present invention is directed to a method for identifying a Luminal B-like HER2 positive tumor in a mammalian subject, which comprises measuring in the blood sample obtained from the subject the amount of at least one acyl carnitine containing at least 10 carbon atoms in the molecule, at least one PC aa, at least one PC ae containing a maximum of 3 unsaturations, and at least one amino acid.

In another preferred embodiment, the present invention is directed to a method for identifying a ER2-positive tumor in a mammalian subject, which comprises measuring in the blood sample obtained from the subject the amount of at least one acyl carnitine containing at least 10 carbon atoms in the molecule, at least one PC aa containing a maximum of 3 unsaturations, at least one amino acid, and at least one lyso PC a.

In another preferred embodiment, the present invention is directed to a method for identifying a Triple negative tumor in a mammalian subject, which comprises measuring in the blood sample obtained from the subject the amount of at least one acyl carnitine containing at least 10 carbon atoms in the molecule, at least one PC aa containing a maximum of 3 unsaturations, at least one amino acid, and at least one lyso PC a.

In another preferred embodiment, the present invention is directed to a method for identifying a HER 2 overexpressing tumor (HER2-positive and Luminal B HER2-positive) in a mammalian subject, which comprises measuring in the blood sample obtained from the subject the amount of at least one acyl carnitine containing at least 10 carbon atoms in the molecule, at least one PC ae, and at least one PC aa.

As certain subtypes of tumors differ from each other with respect to their response to chemotherapy, e.g. it can be differentiated between high response versus low response, the method of the present invention according to this preferred embodiment allows for prediction of whether a patient is likely to respond to chemotherapy, such as neo-adjuvant chemotherapy, even in advance of the therapy. Thus, therapy of breast cancer can be individualized on the basis of the patient's type of tumor. As a consequence, success of chemotherapy can be greatly increased.

Kit

Moreover the invention is also directed to a kit adapted for carrying out the methods as described above wherein the kit comprises a device which device contains one or more wells and one or more inserts impregnated with at least one internal standard. Such a device is in detail described in WO 2007/003344 and WO 2007/003343 which applications are both incorporated herein by reference.

The following examples further describe and clarify the present invention without being intended to limit the scope in any way.

EXAMPLES

General Information:
Patients and Methods

A total of 64 plasma samples of stage III breast cancer women with no previous treatment were included in parallel to three sets of controls. The first one with 93 healthy women used during discovery phase. The second one was analyzed in an independent validation set with 30 plasma samples from breast cancer women as well as 24 controls. Finally the third one with 616 volunteers being 524 healthy participants together with 92 samples (being 55 from colon cancer and 37 from HIV patients) to check the specificity of the results.

Initial tumor dimensions had a mean of 7.09 cm (3.5 cm to 14 cm) and were calculated using clinical and radiological measurements before surgery. Final tumor volume was evaluated, directly on the surgery product, by a dedicated pathologist and pCR was defined as no histopathologic evidence of any residual invasive and or noninvasive residual in breast or nodes (ypT0/ypN0). Patients, with at least 90% response in breast, with no residual tumor in axilla, were then named "High Responders" (Hresp) and compared to the remaining patients named "Low Responders" (Lresp). In order to identify metabolites associated with pCR, the first 29 included patients were used for predictive marker discovery during training and the next 30 were accessible as an independent validation set.

To identify metabolites connected with stable disease/progression (SDPR), all patients were included with a maximum clinical response of 30%, which comprised 12 stable disease and 7 progressions. Training set was assembled using the first 21 admitted patients during discovery of predictive metabolic markers and the remaining 38 patients were available as an independent validation set.

In order to test whether the predictive models were correlated not only, to high and low response rates but, instead, with different degrees of tumor response, the results were validated by analyzing specific metabolites according to progressive degrees of tumor response (0%, 30%, 30-75%, 75-90%, 90-99% and 100%) or SDPR (0-30%), Lresp (30-90%), Hresp (>90%), pCR (100%). In parallel, it was attempted to support additional confirmation on the oncogenic nature of the identified metabolites, therefore they were also tested in a progressive gradient of initial tumor volumes starting from groups with tumor size of 4 cm until 12 cm.

Finally, in order to evaluate whether blood metabolites could be predictive of chemotherapy response, in view of individual subtypes of breast cancer, the patients were divided, first, in their cancer-intrinsic subtypes according to Minckwitz et al (2012) and second according to tumor response rates in Highly Responsive (Hresp, more than 75%) and Low Responsive (Lresp, less than 75%) tumors.

Metabolite Measurements

1. Untargeted Shotgun Exploratory MS/MS Analysis was performed on an independent service at the AB-Sciex Laboratory located in Sao Paulo, SP, Brazil. Plasma samples were injected onto a Shimadzu Prominence LC system coupled to an AB-Sciex 5600 Triple TOF mass spectrometer instrument with an acquisition scan rate of 100 spectra/sec and stable mass accuracy of −2 ppm. Flow Injection Analysis (FIA) was performed using isocratic elution with Methanol/Water (90/10) with 5.0 mM of ammonium formate. Flow rate and injection volumes were 0.025 mL/min and 50 µL respectively. No ion source or declustering potential (50 V and −40 V) optimization was performed. The following ionization parameters were applied: CUR=20 psi, GS1=20 psi, GS2=15 psi, Temp=250° C., IS=5000 V (−4000V). MS scan ranging from m/z 100 to 1200 with accumulation time of 0.25 s and product ion scan from m/z 100 to 1200 and accumulation time of 0.03 s were the adopted parameters during survey and dependent scans respectively.

2. Targeted (ESI-MS/MS) Quantitative Metabolomics/Lipidomics profiling, was performed in an independent validation set with 34 plasma samples from breast cancer women as well as 616 controls, on two independent, fee-for-service basis using quantitative metabolomics platform at Biocrates Life Sciences AG, Innsbruck, Austria and Quest Diagnostics Nichols Institute San Juan Capistrano, Calif., USA. The Targeted (ESI) MS/MS Quantitative technique is described in detail in US 2007/0004044. Briefly, a targeted profiling scheme is used to quantitatively screen for known small molecule metabolites using multiple reaction monitoring, neutral loss and precursor ion scans. Quantification of the metabolites of the biological sample is achieved by reference to appropriate internal standards and the method has been proven to be in conformance with 21 CFR (Code of Federal Regulations) Part 11, which implies proof of reproducibility within a given error range. Concentrations of all analyzed metabolites were reported in Metabolite Panel In total, 183 different metabolites have been detected being 40 acylcanitines, 19 proteinogenic aminoacids, ornithine and citrulline, 19 biogenic amines, sum of Hexoses, 76 phosphatidylcholines, 14 lyso-phosphatidylcholines and 15 sphingomyelins.

Glycerophospholipids are further differentiated with respect to the presence of ester (a) and ether (e) bonds in the glycerol moiety, where two letters (aa=diacyl, ae=acyl-alkyl, ee=dialkyl) denote that two glycerol positions are bound to a fatty acid residue, while a single letter (a=acyl or e=alkyl) indicates the presence of a single fatty acid residue.

Lipid side chain composition is abbreviated as Cx:y, where x denotes the number of carbons in the side chain and y the number of double bonds. E.g. "PC ae C38:1" denotes a plasmalogen/plasmenogen phosphatidylcholine with 38 carbons in the two fatty acid side chains and a single double bond in one of them.

Data Analysis

Training cases were used for marker discovery and to identify any clinical variable that might be associated with response by logistic regression analysis. Quantification of metabolite concentrations and quality control assessment was performed with the MetIDQ® software package (BIOCRATES Life Sciences AG, Innsbruck, Austria). Internal standards serve as the reference for the metabolite concentration calculations. An xls file was then exported, which contained sample names, metabolite names and metabolite concentration with the unit of µmol/L of in plasma.

Data was then uploaded into the web-based analytical pipeline MetaboAnalyst 2.0 (www.metaboanalyst.ca) and normalized using MetaboAnalyst's normalization protocols (Xia et al 2012) for uni and multivariate analysis, high dimensional feature selection, clustering and supervised classification, functional enrichment as well as metabolic pathway analysis.

Data was also imported to ROCCET (ROC Curve Explorer & Tester) available at http://www.roccet.ca/ROCCET/ for the generation of uni and multivariate Receiver Operating Characteristic (ROC) curves obtained through Support Vector Machine (SVM), Partial Least Squares-Discriminant Analysis (PLS-DA) and Random Forests.

Curves were generated by Monte-Carlo cross validation (MCCV) using balanced subsampling where two thirds (⅔) of the samples were used to evaluate the feature importance. Significant features were then used to build classification models, which were validated on the ⅓ of the samples that were left out. The same procedure was repeated multiple times to calculate the performance and confidence interval of each model.

Definition of Terms (1) Up- and down regulation: An up-regulation means an increase in the concentration of a metabolite, e.g. an increase in the rate of at which this biochemical reaction occurs due to for example a change in enzymatic activity. For a down-regulation it's the other way around.

(2) t-test: The t-test is a statistical hypothesis test and the one used is the one integrated in the MarkerView software and is applied to every variable in the table and determines if the mean for each group is significantly different given the standard deviation and the number of samples, e.g. to find out if there is a real difference between the means (averages) of two different groups.

(3) p-value: The p-value is the probability of obtaining a result at least as extreme as the one that was actually observed, assuming that the null hypothesis (the hypothesis of no change or effect) is true. The p-value is always positive and the smaller the value the lower the probability that it is a change occurrence. A p-value of 0.05 or less rejects the null hypothesis at the 5% level, which means that only 5% of the time the change is a chance occurrence. This is the level set in our tables.

(4) Log-fold change: Log-fold change is defined as the difference between the average log transformed concentrations in each condition. This is a way of describing how much higher or lower the value is in one group compared to another. For example, a log-fold change of 0.3 is "equivalent" to an exp(0.3)=1.34 fold change increase compared to the control (healthier group). Further, a log-fold change of −0.3 is "equivalent" to a exp(−0.3)=0.74=(1/1.34) fold change increase compared to the control or decrease fold change of 1.34 to the disease.

Results:

1. Screening and/or Diagnosis of Breast Cancer

Uni and Multivariate Exploratory ROC Analysis

First, Principal Component Analysis (PCA) and ROC Curve Analysis of discovery (30 patients and 93 Controls) and validation sets 1 (34 patients and 24 controls) and 2 (34 patients and 616 controls) have been performed, which revealed an outstanding reliability of screening and diagnosis, as shown in the following Table 6:

TABLE 6

Correlation analysis between the identified metabolites with breast cancer (64 breast cancer patients vs. 616 controls)

|  | Discovery phase: | Validation phase 1 | Validation phase 2 |
|---|---|---|---|
| AUC | 0.99 (95% CI: 0.972-1) | 0.966 (95% CI: 0.884-1) | 0.995 (95% CI: 0.993-0.999) |
| p-value (after 1000 permutations) | <0.001 | <0.001 | <0.001 |
| Sensitivity (%) | 96.67 | 93.75 | 100.00 |
| Specificity (%) | 97.89 | 95.45 | 98.31 |
| Positive predictive value (%) | 93.55 | 96.77 | 79.07 |
| Negatice predictive value (%) | 98.94 | 91.30 | 100.00 |

The PCA and PLS-DA analysis from the 64 women initially included compared to 616 controls. The existence of highly discriminative blood metabolites between cancer patients compared to controls (p=0.0245 after 2000 permutations test) confirmed the PCA analysis during both sets. The Permutation Test Statistics is depicting pValue<5e-04 after 2000 permutations rounds (8A). This result is confirming, as highly significant, the PLS-DA analysis (8B).

The identified metabolites signature, used for UNI or MULTIVARIATE ANALYSIS, are described in Tables 1 and 2, together with t-Test and correlation studies depicting highly significant p-Values and False Discovery Rates (FDR) for all metabolites (Tables 7 and 8).

TABLE 7

| Metabolite | Breast Cancer Correlation | T-stat | p-value | FDR |
|---|---|---|---|---|
| PC aa C40:1 | 0.84847 | 16.737 | 0.0 | 0.0 |
| PC ae C30:2 | 0.82801 | 15.418 | 0.0 | 0.0 |
| C5:1-DC/PC ae C42:1 | −0.92358 | −25.15 | 3.4194E−47 | 1.9376E−46 |
| Delta 5-6 PcaeBig*/SM C24:1 | −0.92133 | −24.741 | 1.5687E−46 | 6.667E−46 |
| Delta 5-6 PCaeBig/MUFA (SM) | −0.92014 | −24.533 | 3.4276E−46 | 1.1654E−45 |
| Delta 5-6 PCaeBig/Total Non-OH SMs | −0.91962 | −24.443 | 4.8167E−46 | 1.1792E−45 |
| Delta 5-6 PCaeBig/PUFA (SM) | −0.91961 | −24.441 | 4.8556E−46 | 1.1792E−45 |
| Delta 5-6 PCaeBig/SM C18:1 | −0.91796 | −24.16 | 1.4091E−45 | 2.9944E−45 |
| Delta 5-6 PCaeBig/SFA (SM) | −0.91776 | −24.128 | 1.5931E−45 | 3.0093E−45 |
| Delta 5-6 PCaeBig/SM C16:0 | −0.91752 | −24.087 | 1.8563E−45 | 3.1557E−45 |
| Delta 5-6 PCaeBig/SM C18:0 | −0.91578 | −23.803 | 5.5125E−45 | 8.5194E−45 |
| Delta 5-6 PCaeBig/SM (OH) C16:1 | −0.91397 | −23.515 | 1.677E−44 | 2.3758E−44 |
| C5:1-DC/PC aa C40:3 | −0.91344 | −23.432 | 2.3158E−44 | 3.0283E−44 |
| C5:1-DC/PC aa C40:1 | −0.91077 | −23.028 | 1.1257E−43 | 1.3294E−43 |
| Delta 5-6 PCaeBig/SM C24:0 | −0.9107 | −23.017 | 1.173E−43 | 1.3294E−43 |
| C5:1-DC/PC aa C40:2 | −0.83807 | −16.038 | 1.8752E−30 | 1.9924E−30 |
| Delta 5-6 PCaeBig/Total OH-SMs | −0.81535 | −14.703 | 1.2526E−27 | 1.2526E−27 |

*Sum arachidonic PUFA PC ae/Sum arachidonic MUFA PC ae

TABLE 8

|  | p-value | −log10(p) | FDR |
|---|---|---|---|
| C5:1-DC/PC ae C42:1 | 3.4194E−47 | 46.466 | 5.8129E−46 |
| Delta 5-6 PCaeBig*/SM C24:1 | 1.5687E−46 | 45.804 | 1.3334E−45 |
| Delta 5-6 PCaeBig/MUFA (SM) | 3.4276E−46 | 45.465 | 1.6509E−45 |
| Delta 5-6 PCaeBig/Total Non-OH SMs | 4.8167E−46 | 45.317 | 1.6509E−45 |
| Delta 5-6 PCaeBig/PUFA (SM) | 4.8556E−46 | 45.314 | 1.6509E−45 |
| Delta 5-6 PCaeBig/SM C18:1 | 1.4091E−45 | 44.851 | 3.869E−45 |
| Delta 5-6 PCaeBig/SFA (SM) | 1.5931E−45 | 44.798 | 3.869E−45 |
| Delta 5-6 PCaeBig/SM C16:0 | 1.8563E−45 | 44.731 | 3.9446E−45 |
| Delta 5-6 PCaeBig/SM C18:0 | 5.5125E−45 | 44.259 | 1.0413E−44 |
| Delta 5-6 PCaeBig/SM (OH) C16:1 | 1.677E−44 | 43.775 | 2.851E−44 |
| C5:1-DC/PC aa C40:3 | 2.3158E−44 | 43.635 | 3.5789E−44 |
| C5:1-DC/PC aa C40:1 | 1.1257E−43 | 42.949 | 1.5339E−43 |
| Delta 5-6 PCaeBig/SM C24:0 | 1.173E−43 | 42.931 | 1.5339E−43 |
| PC aa C40:1 | 6.778E−32 | 31.169 | 8.2305E−32 |
| C5:1-DC/PC aa C40:2 | 1.8752E−30 | 29.727 | 2.1252E−30 |
| PC ae C30:2 | 3.7552E−29 | 28.425 | 3.9899E−29 |
| Delta 5-6 PCaeBig/Total OH-SMs | 1.2526E−27 | 26.902 | 1.2526E−27 |

*Sum arachidonic PUFA PC ae/Sum arachidonic MUFA PC ae

The multivariate ROC curve evaluation obtained during training and validation sets to access the performance of the results for screening purposes are shown in Table 6. The identified metabolites accurately segregate cancer patients from controls with sensitivity=100%, specificity=98.31%, positive predictive value (PPV)=79.09% and negative predictive value (NPV)=100%.

Importantly, even after 1000 rounds of permutation the signatures remained highly significant confirming the ROC curve analysis.

The correlation analysis did not show any significant result between tumor response rate with clinical and pathological variables, as shown in the following Table 9.

TABLE 9

| Parameter | Correlation | p-Value |
|---|---|---|
| ER Status | −0.092498 | 0.48594 |
| PR Status | −0.0086648 | 0.94807 |
| Age | 0.064451 | 0.62769 |
| HER-2 Status | 0.01862 | 0.88868 |
| Nuclear Grade | 0.090079 | 0.49747 |
| Initial Tumor Volume | 0.0016361 | 0.99019 |

Further, ROC curve analyses obtained during the Training Set revealed a minimum set of metabolites for accurately segregating cancer patients from controls comprising at least (a) one amino acid selected from glutamine, glutamate and serine, and one lipid, or (b) glutamine and glutamate. The results obtained from the ROC curve analyses are shown in FIGS. 1 to 7.

FIG. 1A: ROC curve analysis obtained during the Validation Set using two metabolites Glutamine (Gln) and Phosphatidylcholine Acyl-Alkyl C42:1 (PC ae C42:1) with Breast Cancer (n=64) compared to Controls (n=11). CutOff=−9.397, Sensitivity=1.0 (1-1), Specificity=1(1-1), Positive Likelihood Ratio=Infinity, Negative Likelihood Ratio=0.0, T Test=8.0019E-22, pValue<0.001 (1000 permutations).

Figure 1B:
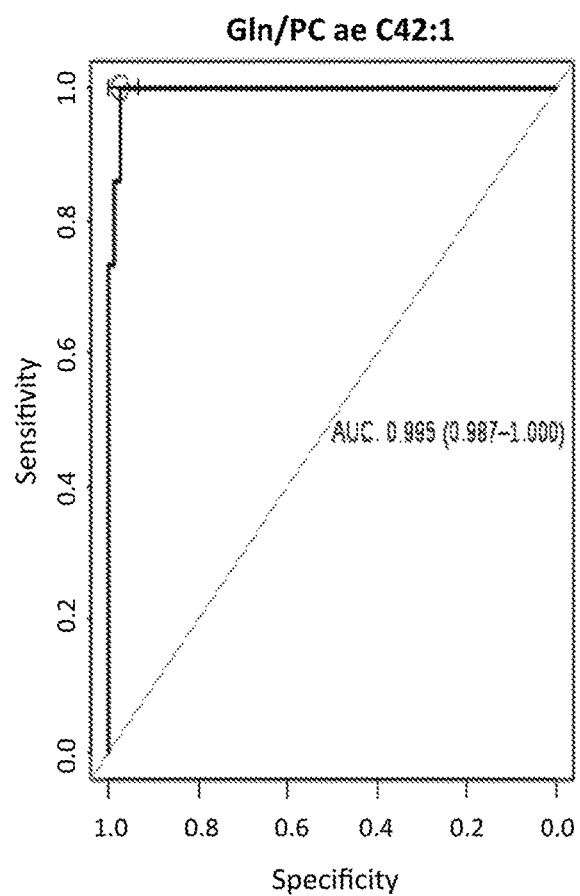
FIG. 1B: ROC curve analysis obtained during the Validation Set using two metabolites Glutamine (Gln) and Phosphatidylcholine Acyl-Alkyl C42:1 (PC ae C42:1).

FIG. 1B: ROC curve analysis obtained during the Validation Set using two metabolites Glutamine (Gln) and Phosphatidylcholine Acyl-Alkyl C42:1 (PC ae C42:1) with Breast Cancer (n=64) compared to Controls (n=77). CutOff=−9.397, Sensitivity=1.0 (1-1), Specificity=) 0.974 (0.935-1), Positive Likelihood Ratio=38.5, Negative Likelihood Ratio=0.0 T Test=1.2632E-58, pValue<0.001 (1000 permutations).

Figure 2A:
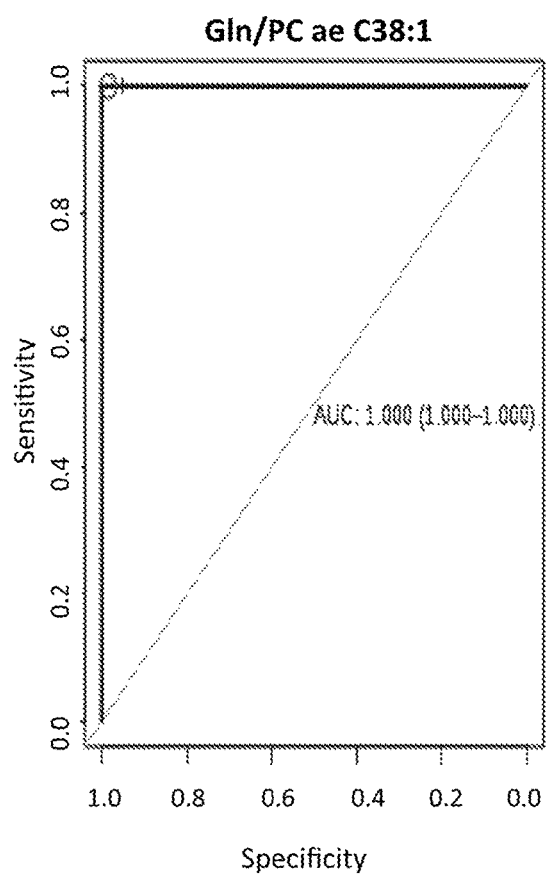
FIG. 2A: ROC curve analysis obtained during the Training Set using two metabolites Glutamine (Gln) and Phosphatidylcholine Acyl-Alkyl C38:1 (PC ae C38:1).

FIG. 2A: ROC curve analysis obtained during the Training Set using two metabolites Glutamine (Gln) and Phosphatidylcholine Acyl-Alkyl C38:1 (PC ae C38:1) with Breast Cancer (n=64) compared to Controls (n=11). CutOff=−6.645, Sensitivity=1.0 (1-1), Specificity=0.9844 (0.953-1)), Positive Likelihood Ratio=64.0, Negative Likelihood Ratio=0.0, T Test=9.9636E-31 pValue<0.001 (1000 permutations).

Figure 2B:
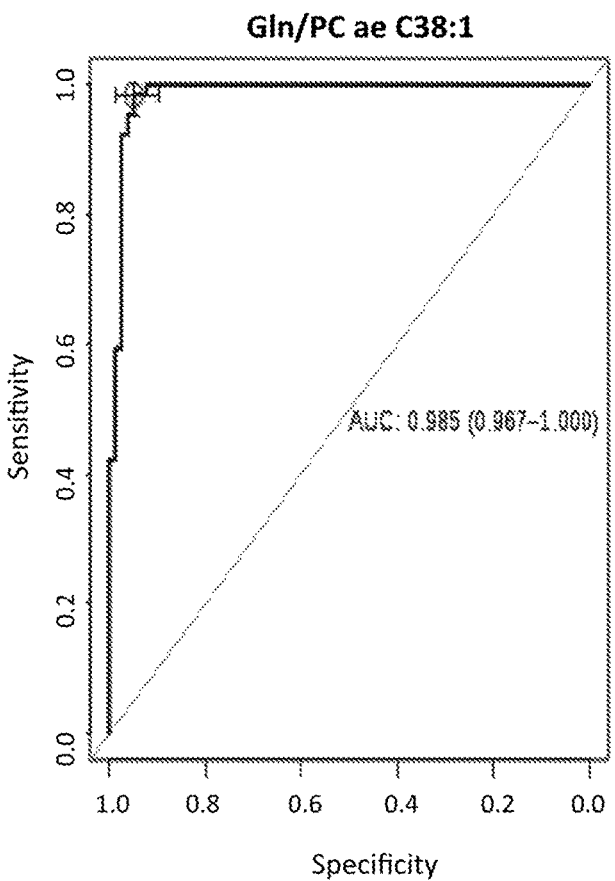
FIG. 2B: ROC curve analysis obtained during the Validation Set using two metabolites Glutamine (Gln) and Phosphatidylcholine Acyl-Alkyl C38:1 (PC ae C38:1).

FIG. 2B: ROC curve analysis obtained during the Validation Set using two metabolites Glutamine (Gln) and Phosphatidylcholine Acyl-Alkyl C38:1 (PC ae C38:1) with Breast Cancer (n=64) compared to Controls (n=77). CutOff=−6.645, Sensitivity=0.9844 (0.953-1), Specificity=0.9481 (0.896-0.967), Positive Likelihood Ratio=18.95, Negative Likelihood Ratio=0.01648, T Test=3.6347E-42, pValue<0.001 (1000 permutations).

Figure 3A:
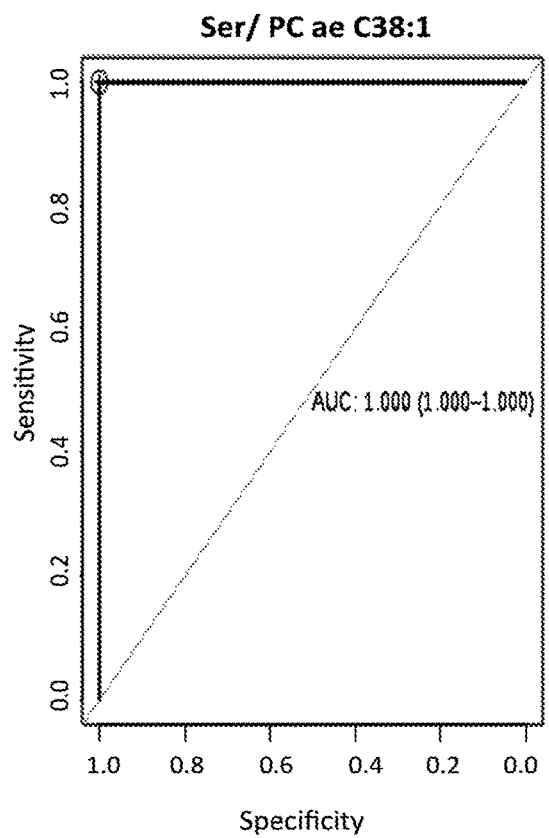
FIG. 3A: ROC curve analysis obtained during the Training Set using two metabolites Serine (Ser) and Phosphatidylcholine Acyl-Alkyl C38:1 (PC ae C38:1).

FIG. 3A: ROC curve analysis obtained during the Training Set using two metabolites Serine (Ser) and Phosphatidylcholine Acyl-Alkyl C38:1 (PC ae C38:1) with Breast Cancer (n=64) compared to Controls (n=11). CutOff=6.231, Sensitivity=1.0 (1-1), Specificity=1.0 (1-1), Positive Likelihood Ratio=Infinity, Negative Likelihood Ratio=0.0, T Test=1.9204E-13, pValue<0.001 (1000 permutations)

Figure 3B:
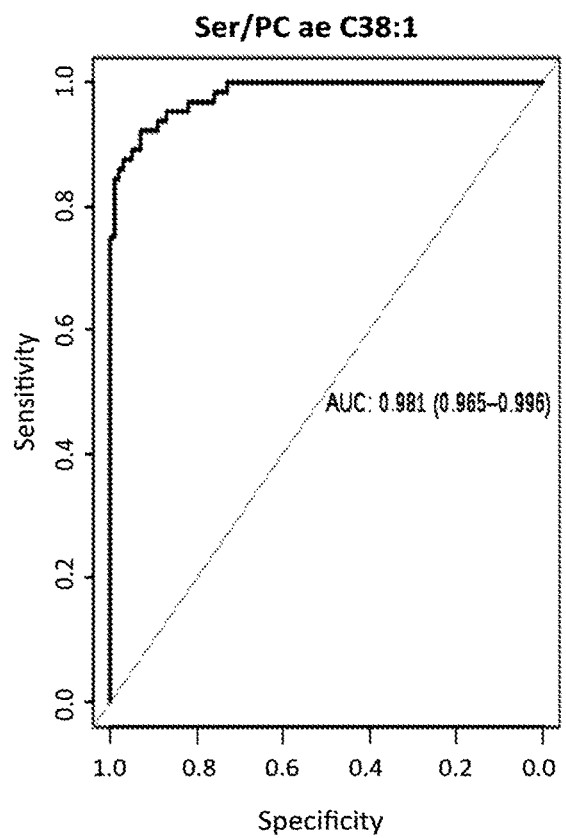
FIG. 3B: ROC curve analysis obtained during the Validation Set using two metabolites Serine (Ser) and Phosphatidylcholine Acyl-Alkyl C38:1 (PC ae C38:1).

FIG. 3B: ROC curve analysis obtained during the Validation Set using two metabolites Serine (Ser) and Phosphatidylcholine Acyl-Alkyl C38:1 (PC ae C38:1) with Breast Cancer (n=64) compared to Controls (n=77). CutOff=5.575, Sensitivity=0.9219 (0.851-0.969), Specificity=0.93 (0.885-0.98), Positive Likelihood Ratio=13.17, Negative Likelihood Ratio=0.08401, T Test=1.6951E-43, pValue<0.001 (1000 permutations).

Figure 4A:
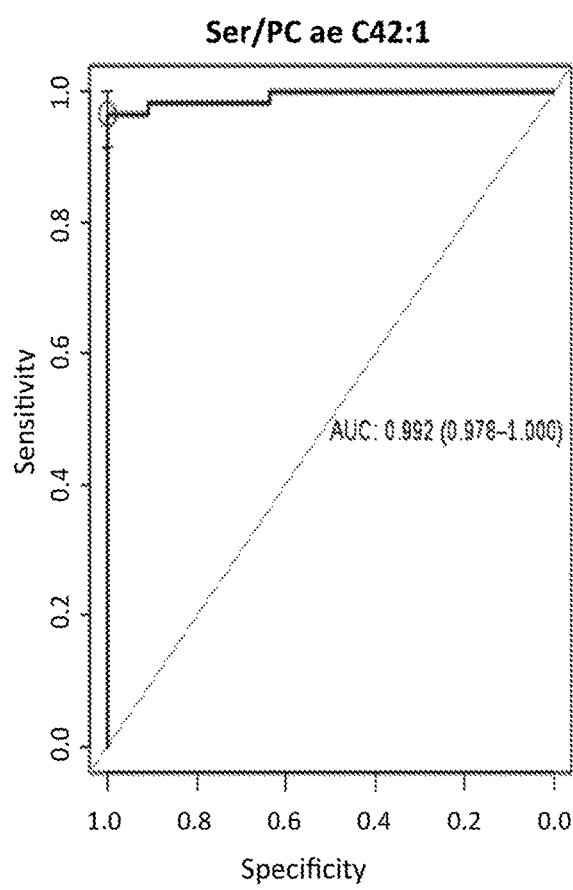
FIG. 4A: ROC curve analysis obtained during the Training Set using two metabolites Serine (Ser) and Phosphatidylcholine Acyl-Alkyl C42:1 (PC ae C42:1).

FIG. 4A: ROC curve analysis obtained during the Training Set using two metabolites Serine (Ser) and Phosphatidylcholine Acyl-Alkyl C42:1 (PC ae C42:1) with Breast Cancer (n=64) compared to Controls (n=11). CutOff=7.468, Sensitivity=0.9655 (0.914-1), Specificity=1.0 (1-1), Positive Likelihood Ratio=Infinity, Negative Likelihood Ratio=0.03448, T Test=3.7077E-10, pValue<0.001 (1000 permutations).

Figure 4B:
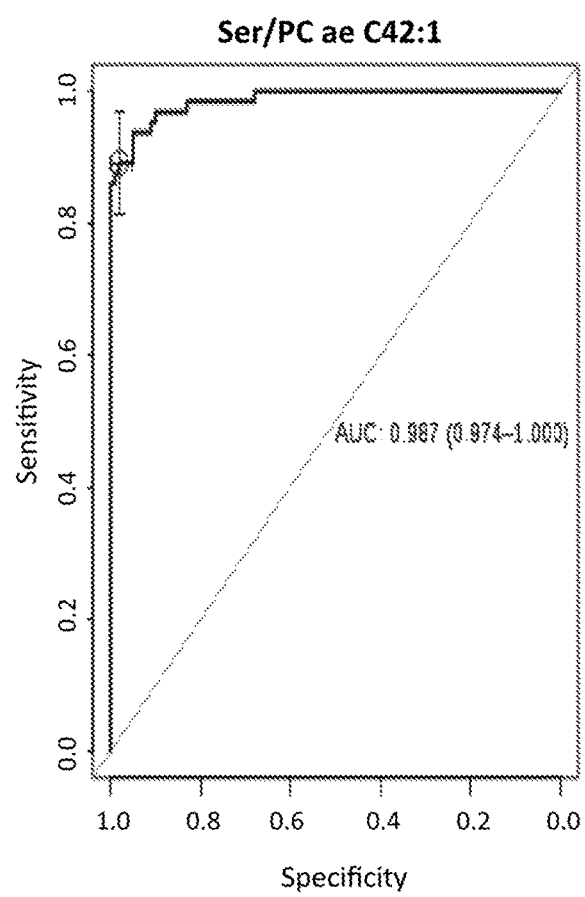
FIG. 4B: ROC curve analysis obtained during the Validation Set using two metabolites Serine (Ser) and Phosphatidylcholine Acyl-Alkyl C42:1 (PC ae C42:1).

FIG. 4B: ROC curve analysis obtained during the Validation Set using two metabolites Serine (Ser) and Phosphatidylcholine Acyl-Alkyl C42:1 (PC ae C42:1) with Breast Cancer (n=64) compared to Controls (n=77). CutOff=7.162, Sensitivity=0.8906 (0.812-0.969) Specificity=0.98 (0.95-1), Positive Likelihood Ratio=44.53 Negative Likelihood Ratio=0.1116, T Test=1.6951E-43, pValue<0.001 (1000 permutations).

Figure 5A:
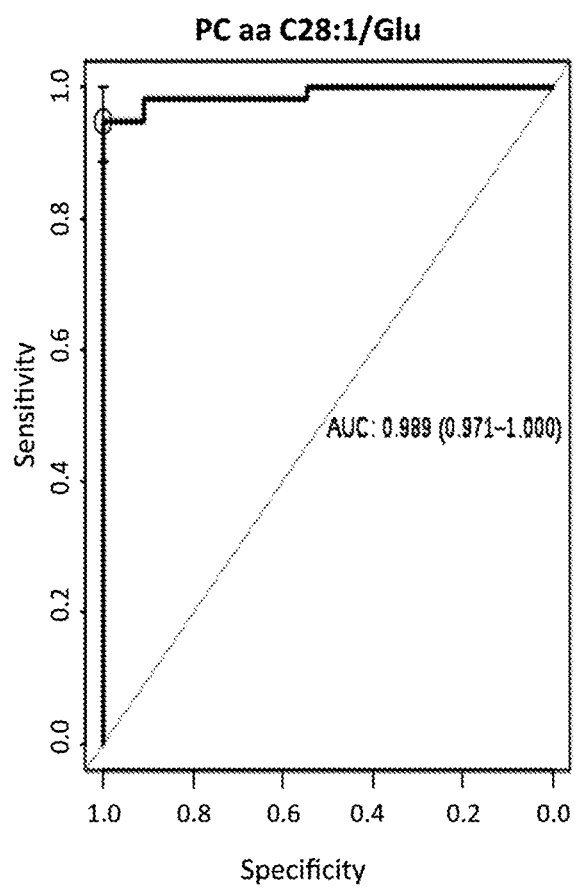
FIG. 5A: ROC curve analysis obtained during the Training Set using two metabolites Glutamate (Glu) and Phosphatidylcholine Acyl-Acyl C28:1 (PC aa C28:1).

FIG. 5A: ROC curve analysis obtained during the Training Set using two metabolites Glutamate (Glu) and Phosphatidylcholine Acyl-Acyl C28:1 (PC aa C28:1) with Breast Cancer (n=64) compared to Controls (n=11). CutOff=−6.119, Sensitivity=0.9483 (0.888-1), Specificity=1.0 (1-1), Positive Likelihood Ratio=Infinity, Negative Likelihood Ratio=0.05172, T Test=4.1972E-20, pValue<0.001 (1000 permutations).

Figure 5B:
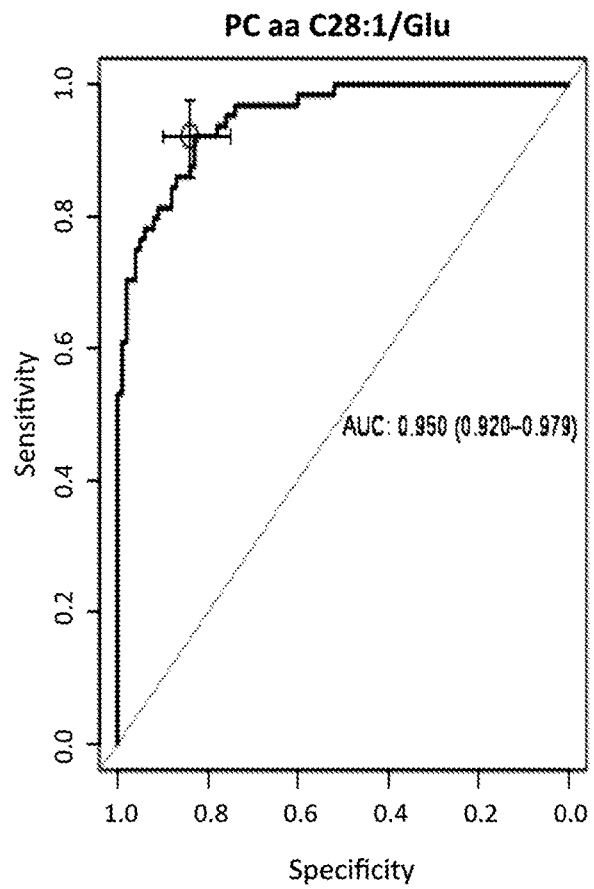
FIG. 5B: ROC curve analysis obtained during the Validation Set using two metabolites Glutamate (Glu) and Phosphatidylcholine Acyl-Acyl C28:1 (PC aa C28:1).

FIG. 5B: ROC curve analysis obtained during the Validation Set using two metabolites Glutamate (Glu) and Phosphatidylcholine Acyl-Acyl C28:1 (PC aa C28:1) with Breast Cancer (n=64) compared to Controls (n=77). CutOff=−6.335, Sensitivity=0.9219 (0.859-0.977), Specificity=0.83 (0.75-0.9), Positive Likelihood Ratio=5.423, Negative Likelihood Ratio=0.09413, T Test=2.1657E-26, pValue<0.001 (1000 permutations).

FIG. 6A: ROC curve analysis obtained during the Training Set using two metabolites Glutamate (Glu) and Phosphatidylcholine Acyl-Alkyl C42:1 (PC ae C42:1) with Breast Cancer (n=64) compared to Controls (n=11). Sensitivity=100%, Specificity=100%, Positive Predictive Value=100%, Negative Predictive Value=100%, pValue<0.001 (1000 permutations).

FIG. 6B: ROC curve analysis obtained during the Validation Set using two metabolites Glutamate (Glu) and Phosphatidylcholine Acyl-Alkyl C42:1 (PC ae C42:1) with Breast Cancer (n=64) compared to Controls (n=77). Sensitivity=100%, Specificity=99%, Positive Predictive Value=98.46%, Negative Predictive Value=100%, pValue<0.001 (1000 permutations).

Figure 7A:
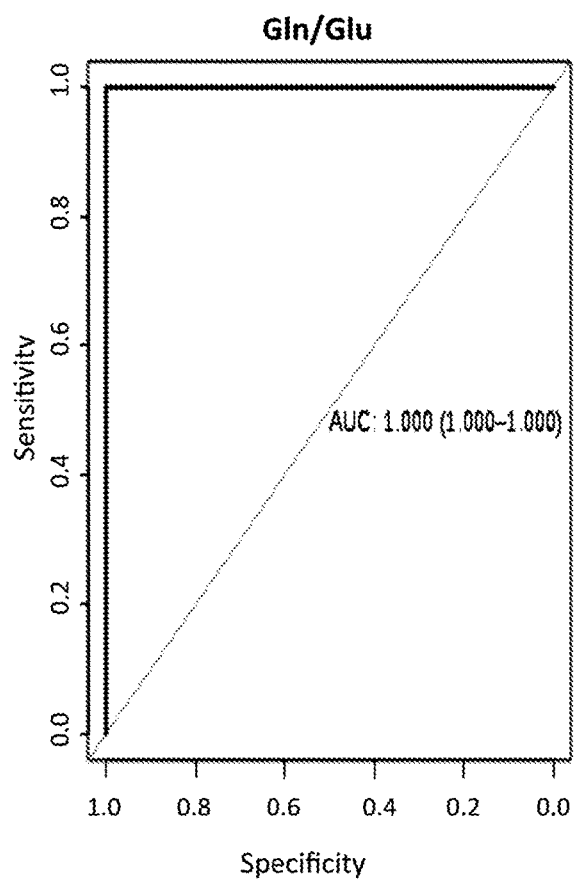
FIG. 7A: ROC curve analysis obtained during the Training Set using two metabolites Glutamate (Glu) and Glutamine (Gln).

FIG. 7A: ROC curve analysis obtained during the Training Set using two metabolites Glutamate (Glu) and Glutamine (Gln) with Breast Cancer (n=64) compared to Controls (n=11). CutOff=−1.101, Sensitivity=1.0(1-1), Specificity=1.1 (1-1), Positive Likelihood Ratio=Infinity, Negative Likelihood Ratio=0.0, T Test=9.9058E-17, pValue<0.001 (1000 permutations).

Figure 7B:
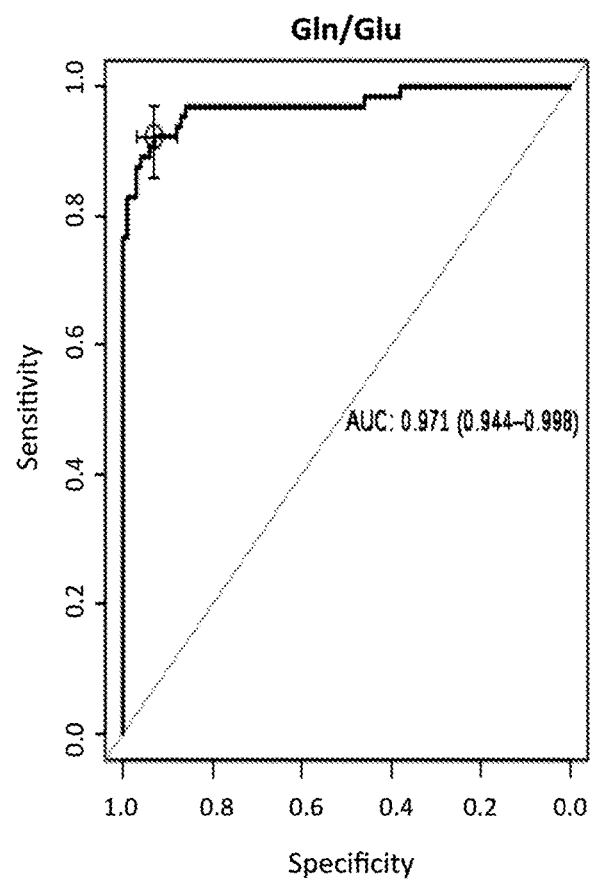
FIG. 7B: ROC curve analysis obtained during the Training Set using two metabolites Glutamate (Glu) and Glutamine (Gln).
Figure 8A:
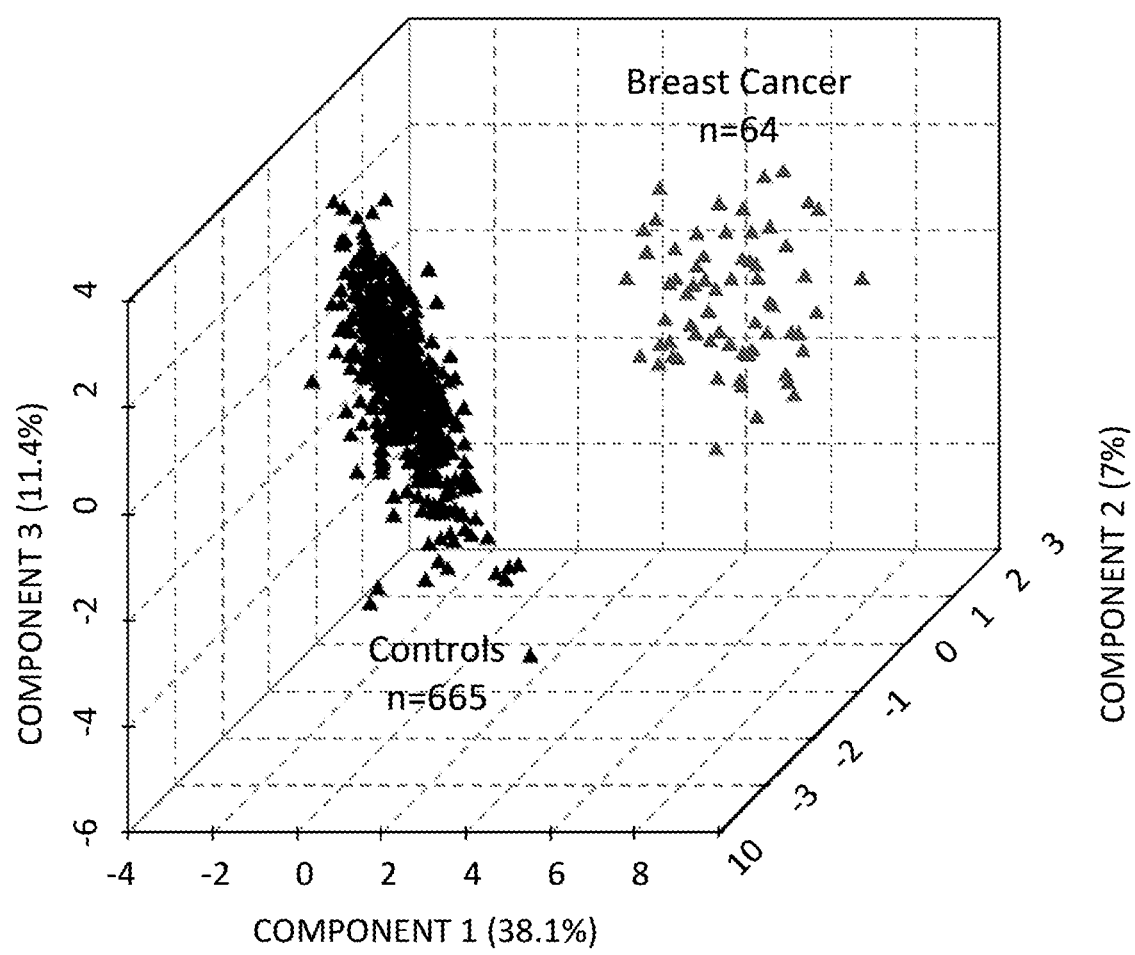
FIGS. 8A and 8B: Final validation set with Breast Cancer compared to Controls.
Figure 8B:
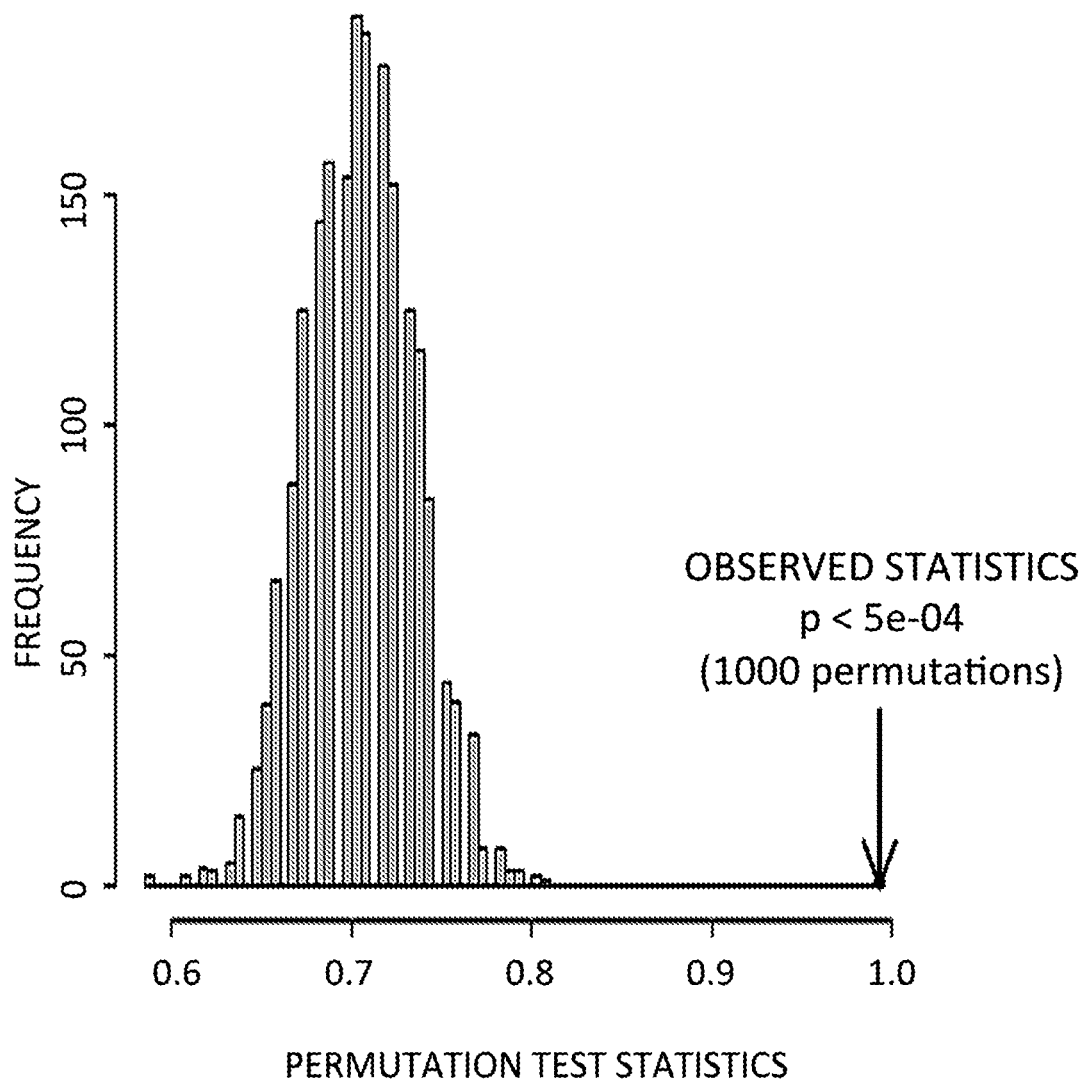

FIG. 7B: ROC curve analysis obtained during the Training Set using two metabolites Glutamate (Glu) and Glutamine (Gln) with Breast Cancer (n=64) compared to Controls (n=77). CutOff=−1.101, Sensitivity=0.9219 (0.851-0.969), Specificity=0.93 (0.86-0.97), Positive Likelihood Ratio=13.17, Negative Likelihood Ratio=0.08401, T Test=4.6268E-40, pValue<0.001 (1000 permutations).

As can be seen by the above data, the present invention allows screening for and diagnosing breast cancer patients with improved accuracy and reliability compared with known methods. This can in particular be depicted by the following comparison (Table 10).

TABLE 10

Comparison of present invention with prior art studies

| Parameter | Present Study n = 665 | Qiu Y et al* n = 80 |
|---|---|---|
| Sensitivity | 100% | 98.1% |
| Specificity | 97.46% | 96.0% |
| Positive Predictive Value | 96.97% | 98.1% |
| Negative Predictive Value | 100.00% | 96.0% |
| Prediction of chemotherapy response | Yes | No |
| Identification of intrinsic subtypes | Yes | No |
| Minimum number of Metabolites | 2 | 3 |

*Qui Y. et al., Int. J. Mol. Sci. 2013, 14, 8047-8061

2. Prediction of High (Hresp) or Low Response (SDPR) to Chemotherapy:

A total of 10 patients achieved at least 90% response (6 in the training and 4 at the validation set), among them 7 patients reached complete pathological response (pCR) defined as ypT0/ypN0. The total percentage of pCR and SDPR was observed in 11.8% (7/59) and 32% (19/59) of patients respectively.

ROC curve analyses obtained during the Training Set revealed a minimum set of metabolites for accurately predicting chemotherapy response comprising at least one amino acid selected from serine and glutamine, methylated arginine, one acyl carnitine and one lipid. The results obtained from the ROC curve analyses are shown in FIGS. 9 to 12.

Figure 9A:
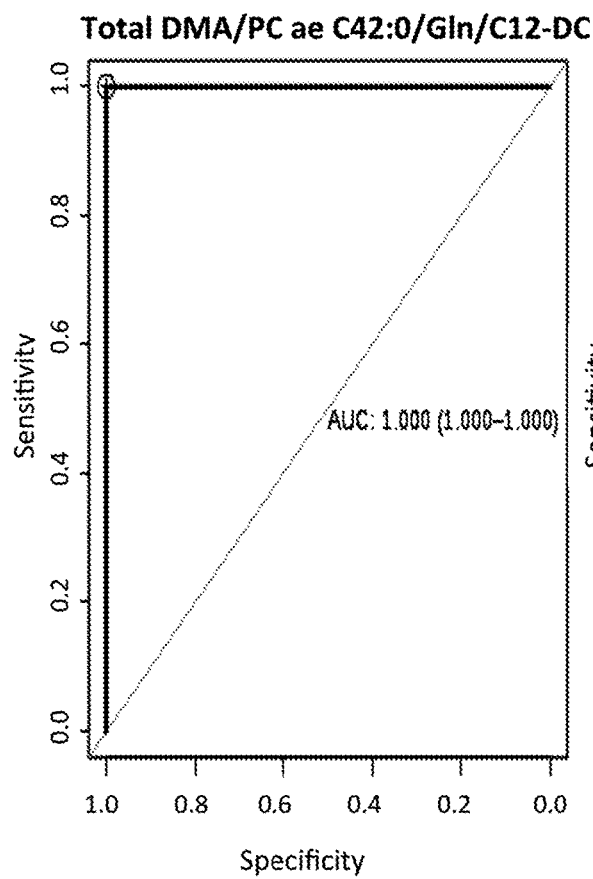
FIG. 9A: ROC curve analysis obtained during the Training Set, using Total DMA, PC ae C42:0, Glutamine (Gln) and Dodecanedioylcarnitine (C12-DC), comparing patients with Complete Pathological Response and patients with 35-78% Response.

FIG. 9A: ROC curve analysis obtained during the Training Set, using Total DMA, PC ae C42:0, Glutamine (Gln) and Dodecanedioylcarnitine (C12-DC), comparing patients with Complete Pathological Response (pCR, n=7) and patients with 35-78% Response (n=21). CutOff=−11.56, Sensitivity=1.0 (1-1), Specificity=1.0 (1-1), Positive Likelihood Ratio=Infinity, Negative Likelihood Ratio=0.0, T Test=8.553E-6, pValue<0.001 (1000 permutations).

Figure 9B:
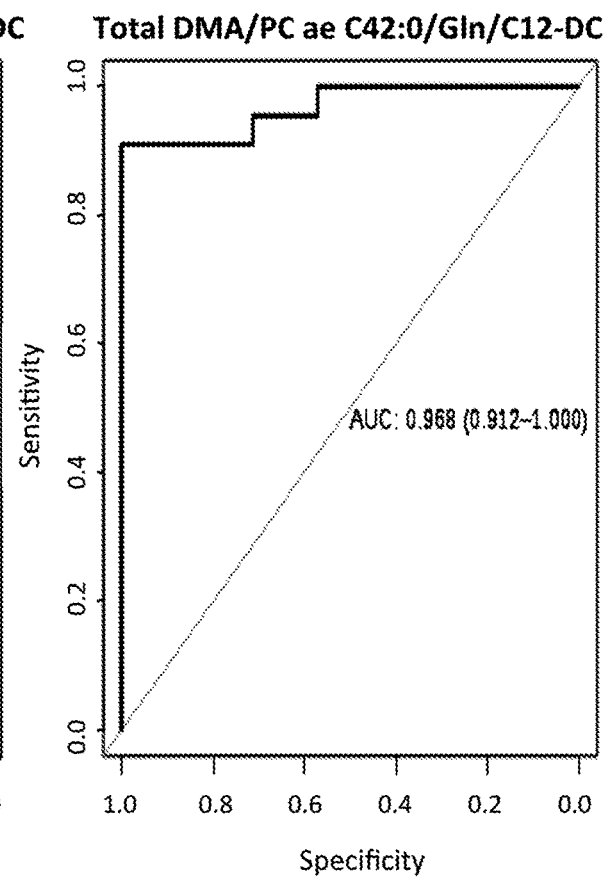
FIG. 9B: ROC curve analysis obtained during the Validation Set, using Total DMA, PC ae C42:0, Glutamine (Gln) and C12-DC, comparing patients with Complete Pathological Response and patients with Stable Disease/Progression.

FIG. 9B: ROC curve analysis obtained during the Validation Set, using Total DMA, PC ae C42:0, Glutamine (Gln) and C12-DC, comparing patients with Complete Pathological Response (pCR, n=7) and patients with Stable Disease/Progression (SDPR, n=22). CutOff=−11.56, Sensitivity=0.9091 (0.773-1), Specificity=1.0 (1-1), Positive Likelihood Ratio=Infinity, Negative Likelihood Ratio=0.09091, T Test=2.5381E-4, pValue<0.001 (1000 permutations).

Figure 10A:
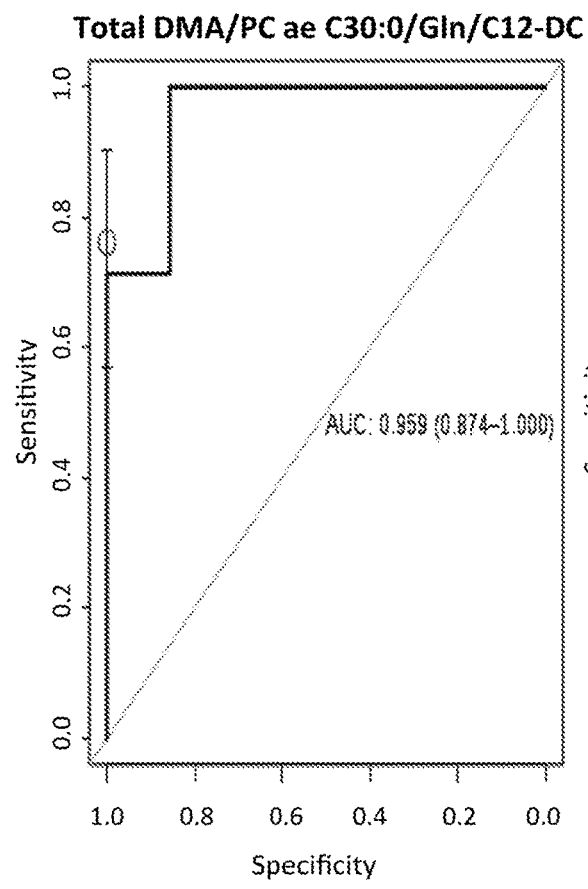
FIG. 10A: ROC curve analysis obtained during the Training Set, using Total DMA, PC ae C30:0, Glutamine (Gin) and C12-DC, comparing patients with Complete Pathological Response and patients with 35-78% Response.

FIG. 10A: ROC curve analysis obtained during the Training Set, using Total DMA, PC ae C30:0, Glutamine (Gln) and C12-DC, comparing patients with Complete Pathological Response (pCR, n=7) and patients with 35-78% Response (n=21). CutOff=−10.12, Sensitivity=0.7143 (0.571-0.905), Specificity=1.0 (1-1), Positive Likelihood Ratio=Infinity, Negative Likelihood Ratio=0.2857, T Test=8.553E-6, pValue<0.001 (1000 permutations).

Figure 10B:
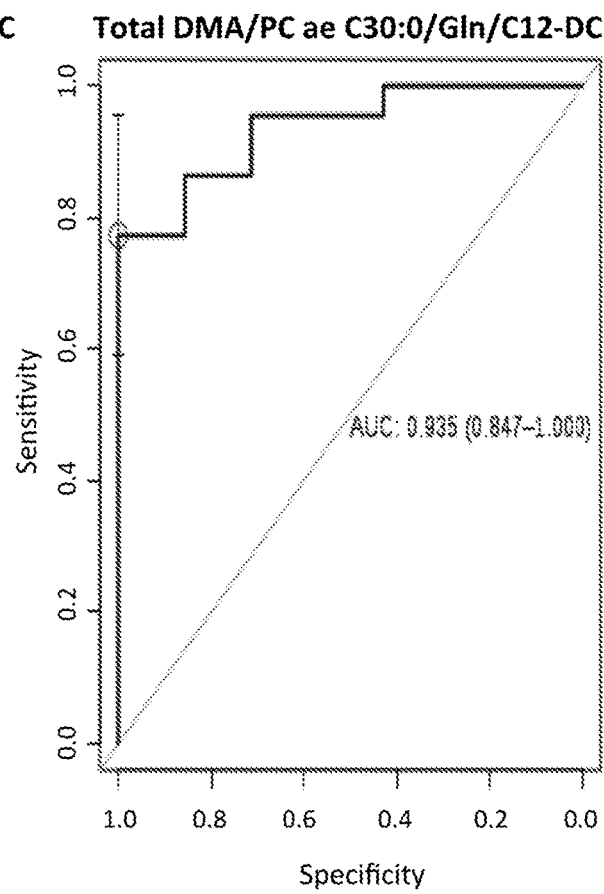
FIG. 10B: ROC curve analysis obtained during the Validation Set using Total DMA, PC ae C30:0, Glutamine (Gin) and C12-DC, comparing patients with Complete Pathological Response and patients with Stable Disease/Progression.

FIG. 10B: ROC curve analysis obtained during the Validation Set using Total DMA, PC ae C30:0, Glutamine (Gln) and C12-DC, comparing patients with Complete Pathological Response (pCR, n=7) and patients with Stable Disease/Progression (SDPR, n=22). CutOff=−10.12, Sensitivity=0.773 (0.591-0.955), Specificity=1.0 (1-1), Positive Likelihood Ratio=Infinity, Negative Likelihood Ratio=0.2273, T Test=4.8125E-4, pValue<0.001 (1000 permutations).

Figure 11A:
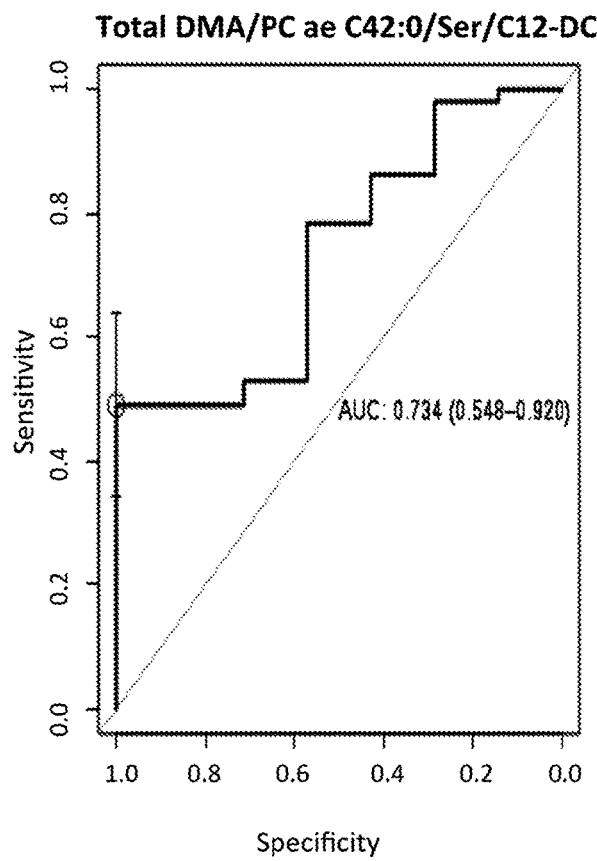
FIG. 11A: ROC curve analysis obtained during the Training Set, using Total DMA, PC ae C42:0, Serine (Ser) and C12-DC, comparing patients with Complete Pathological Response and Low Response patients.

FIG. 11A: ROC curve analysis obtained during the Training Set, using Total DMA, PC ae C42:0, Serine (Ser) and C12-DC, comparing patients with Complete Pathological Response (pCR, n=7) and Low Response patients (n=52). CutOff=8.416, Sensitivity=0.4902 (0.342-0.638) Specificity=1.0 (1-1), Positive Likelihood Ratio=Infinity Negative Likelihood Ratio=0.5098, T Test=0.018905, pValue<0.001 (100 permutations)

Figure 11B:
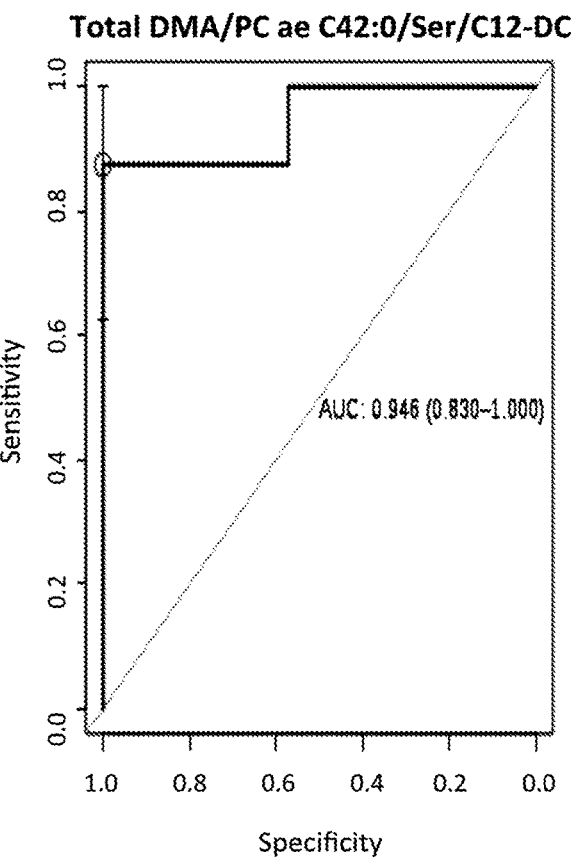
FIG. 11B: ROC curve analysis obtained during the Validation Set, using Total DMA, PC ae C42:0, Serine (Ser) and C12-DC, comparing patients with Complete Pathological Response and patients with Stable Disease/Progression (SDPR).

FIG. 11B: ROC curve analysis obtained during the Validation Set, using Total DMA, PC ae C42:0, Serine (Ser) and C12-DC, comparing patients with Complete Pathological Response (pCR, n=7) and patients with Stable Disease/Progression (SDPR) (n=22). CutOff=−8.412, Sensitivity=0.875 (0.625-1), Specificity=1.0 (1-1), Positive Likelihood Ratio=Infinity, Negative Likelihood Ratio=0.125, T Test=0.013813, pValue<0.001 (100 permutations).

Figure 12A:
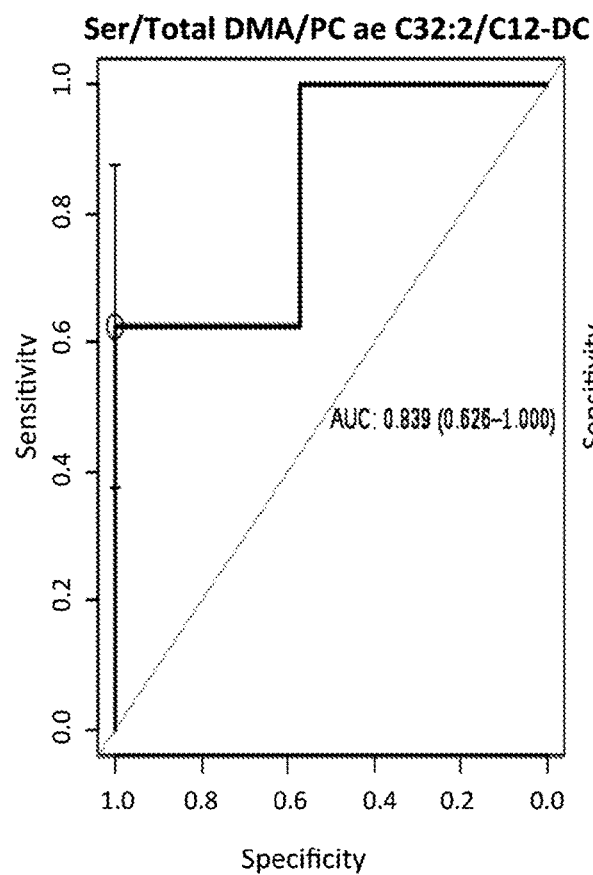
FIG. 12A: ROC curve analysis obtained during the Training Set, using Total DMA, PC ae C32:2, Serine (Ser) and C12-DC, comparing patients with Complete Pathological Response and 80-92%.

FIG. 12A: ROC curve analysis obtained during the Training Set, using Total DMA, PC ae C32:2, Serine (Ser) and C12-DC, comparing patients with Complete Pathological Response (pCR, n=7) and 80-92% (n=8). CutOff=11.38, Sensitivity=0.625 (0.375-0.875) Specificity=1.0 (1-1), Positive Likelihood Ratio=Infinity, Negative Likelihood Ratio=0.375, T Test=0.017765, pValue<0.001 (100 permutations).

Figure 12B:
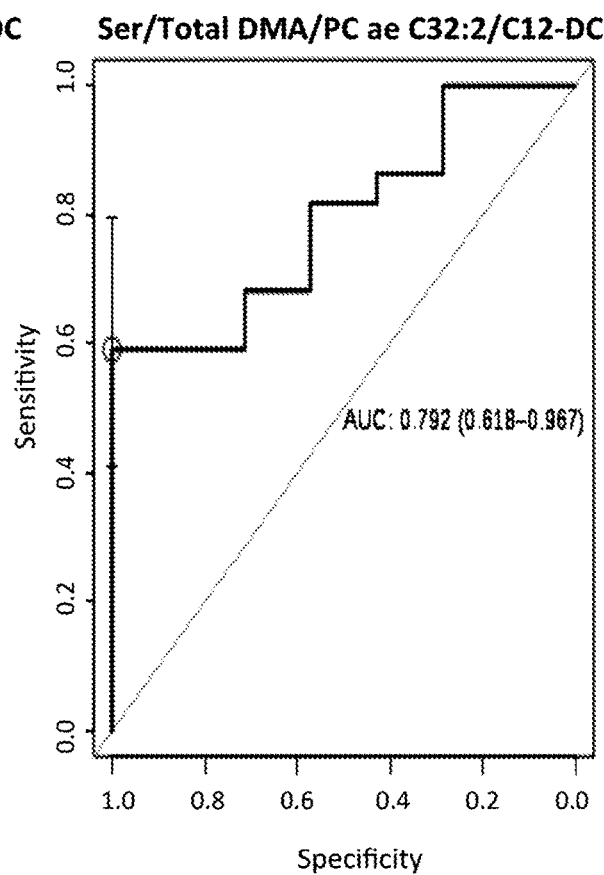
FIG. 12B: ROC curve analysis obtained during the Validation Set, using Total DMA, PC ae C32:2, Serine (Ser) and C12-DC, comparing patients with Complete Pathological Response and patients with Stable Disease/Progression).

FIG. 12B: ROC curve analysis obtained during the Validation Set, using Total DMA, PC ae C32:2, Serine (Ser) and C12-DC, comparing patients with Complete Pathological Response (pCR, n=7) and patients with Stable Disease/Progression (SDPR) (n=22). CutOff=11.37, Sensitivity=0.5909 (0.479-0.797) Specificity=1.0 (1-1), Positive Likelihood Ratio=Infinity Negative Likelihood Ratio=0.4091, T Test=0.026961, pValue<0.001 (100 permutations).

The above data show the outstanding accuracy and reliability of the prediction, as determined by the parameters of specificity, sensitivity, PPV and NPV, by using the above-specified biomarker combinations.

3. Metabolites According to Intrinsic Breast Cancer Subtypes

Figure 14:
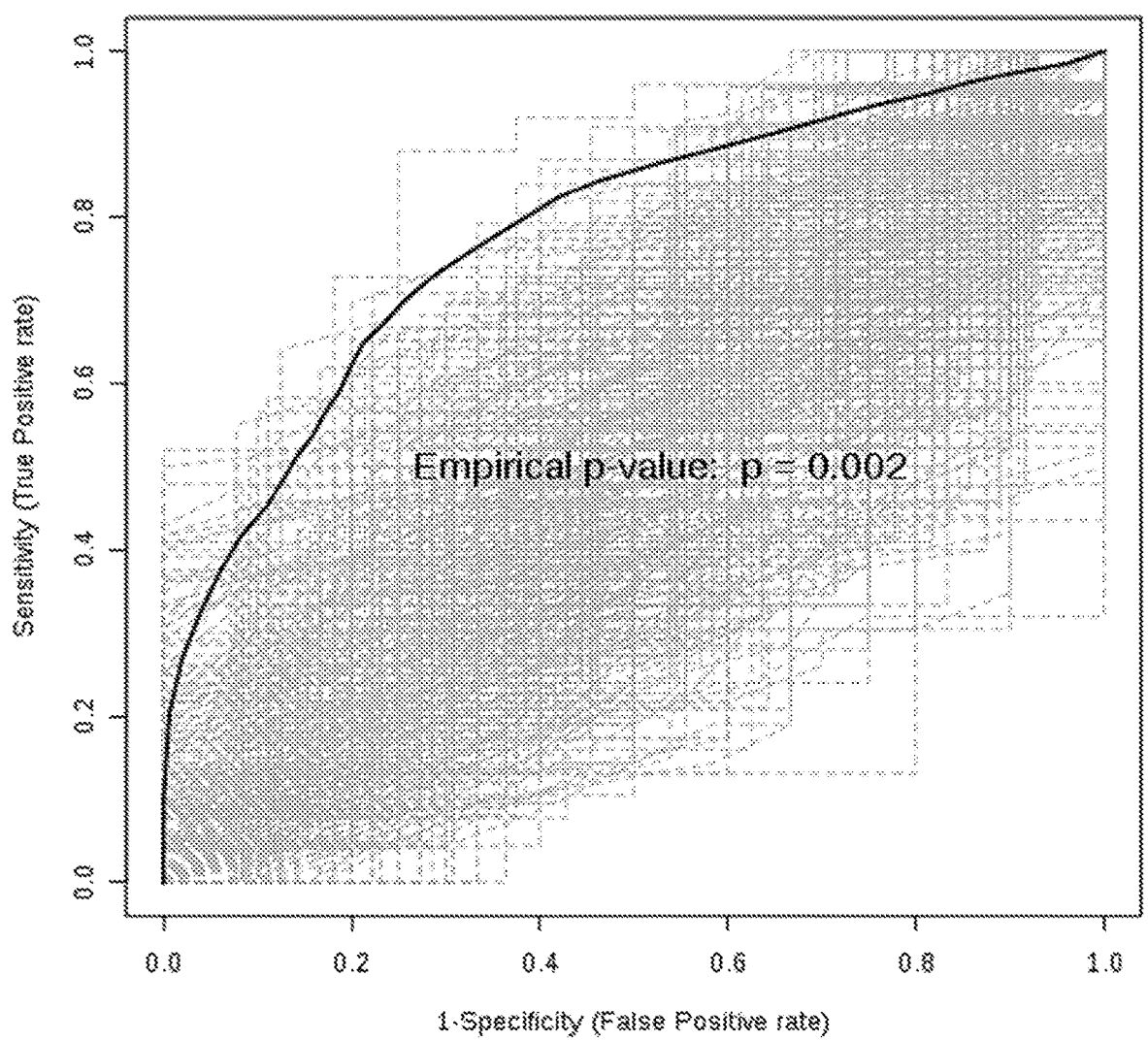
FIG. 14: Identification of specific subtypes of breast cancer using the metabolites depicted in Table 12. ROC curve analysis showing the identification of patients with HER2 Tumors (LumB-HER2+HER2) and patients with Triple Negatives and Luminals A/B.
Figure 15:
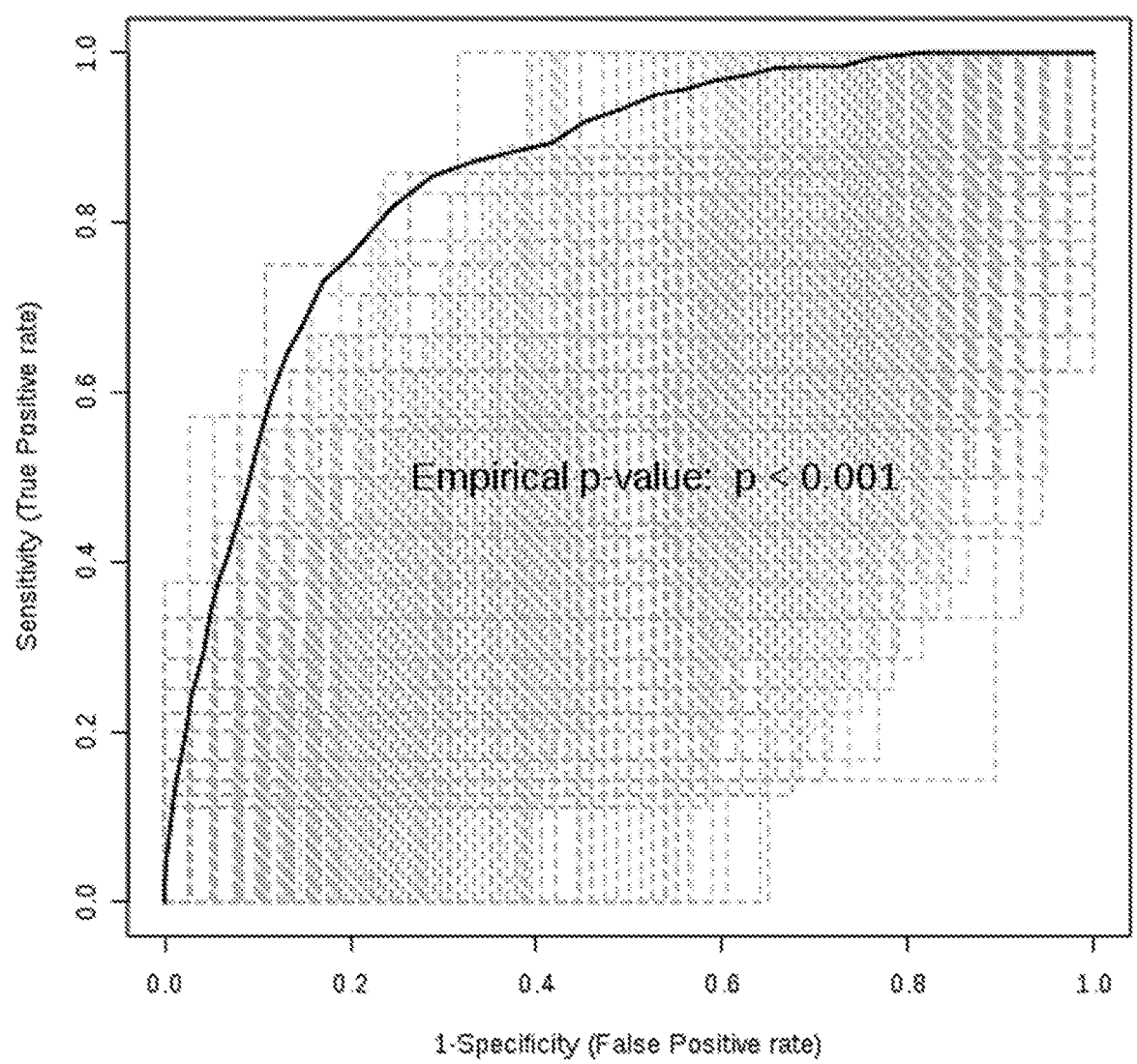
FIG. 15: Identification of specific subtypes of breast cancer using the metabolites depicted in Table 13. ROC curve analysis showing the identification of patients with Triple Negatives and HER2-Positive/Luminals A/B.

ROC curve analyses obtained during the Training Set revealed a minimum set of metabolites for subclassification of breast cancer subtypes comprising at least one acylcarnitine containing at east 10 carbon atoms in the molecule and at least one lipid containing a maximum of 3 unsaturations in the molecule. The results obtained from the ROC curve analyses are shown in FIGS. 13 to 15.

Figure 13:
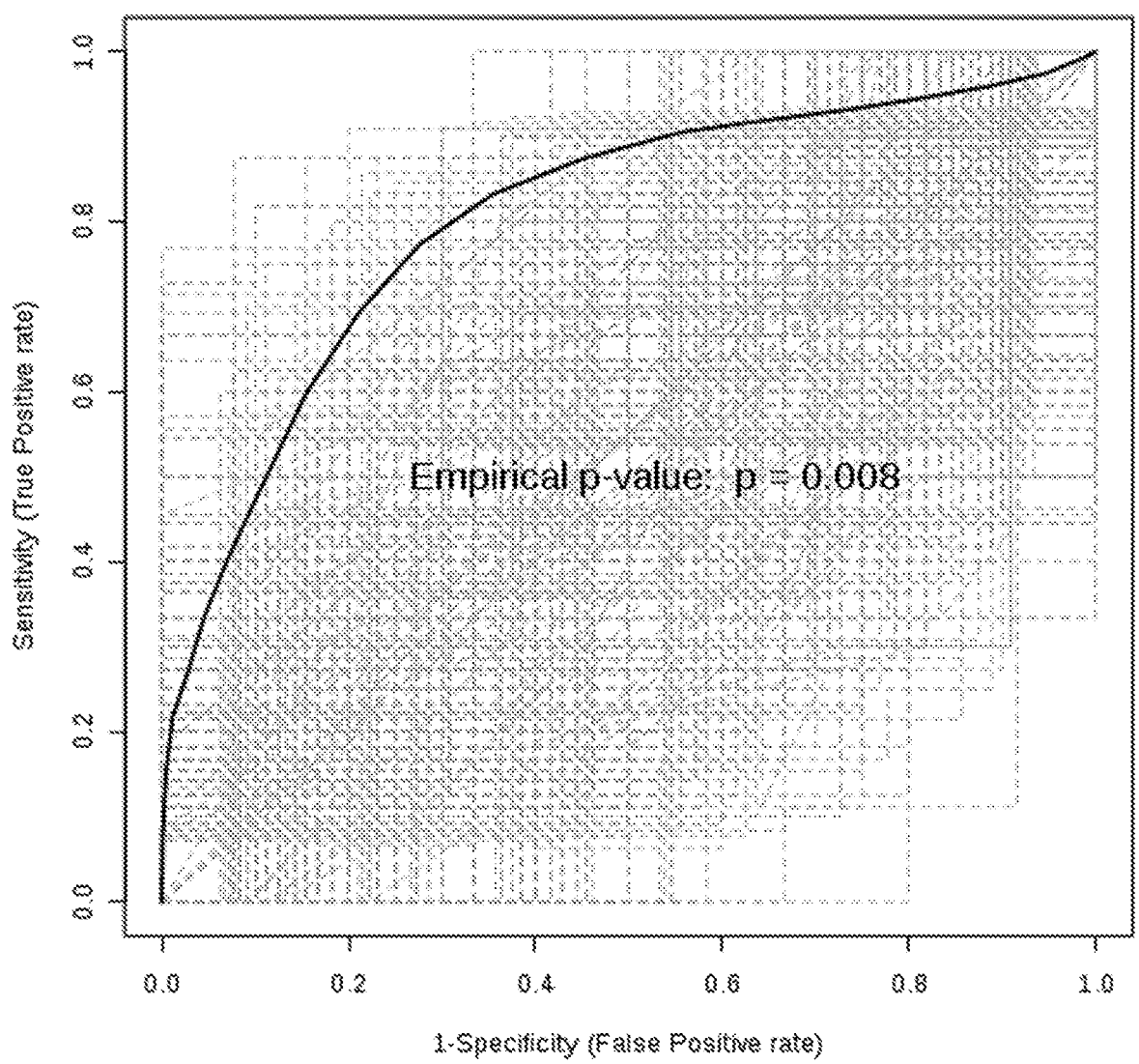
FIG. 13: Identification of specific subtypes of breast cancer using the metabolites depicted in Table 11. ROC curve analysis showing the identification of patients with Luminal Tumors A/B and patients with Triple Negatives and HER2-positives.

FIG. 13: Identification of specific subtypes of breast cancer using the metabolites depicted in Table 11. ROC curve analysis showing the identification of patients with Luminal Tumors A/B (n=30) and patients with Triple Negatives and HER2-positives (Other Tumors n=29). AUC=0.821 (95% CI: 0.686-0.945), Sensitivity=81.08%, Specificity=82.86%, Positive predictive value 83.33%, Negative predictive value 80.56%, p-value=0.008 (1000 permutations).

TABLE 11

List of metabolites used in the Multivariate
Analysis to identify Luminal A/B tumors.

| Metabolites | AUC | pValue |
| --- | --- | --- |
| Lys/C16:1-OH/PC ae C40:1 | 0.81379 | 7.4353E−6 |
| C16:1-OH/PC ae C40:1 | 0.79655 | 4.2815E−5 |
| C16:1-OH/PC ae C40:1 | 0.79195 | 9.1894E−5 |
| lysoPC a C24:0/C9/C10:2 | 0.78966 | 5.8548E−5 |
| C16:1-OH/PC ae C42:0 | 0.78736 | 5.783E−5 |
| C16:1-OH/PC aa C38:0 | 0.78621 | 9.1278E−5 |
| PC ae C30:2/C9/C10:2 | 0.78621 | 4.0237E−5 |
| His/C16:1-OH/PC ae C40:1 | 0.78391 | 8.8153E−5 |

FIG. 14: Identification of specific subtypes of breast cancer using the metabolites depicted in Table 12. ROC curve analysis showing the identification of patients with HER2 Tumors (LumB-HER2+HER2) (n=19) and patients with Triple Negatives and Luminals A/B (Other Tumors n=40). AUC=0.803 (95% CI: 0.639-0.926), Sensitivity=86.36%, Specificity=76.92%, Positive predictive value=61.29%, Negative predictive value=93.02%, p-value=0.002 (1000 permutations).

TABLE 12

List of metabolites used in the Multivariate
Analysis to identify HER2-positive tumors.

| Metabolites | AUC | pValue |
| --- | --- | --- |
| PC aa C26:0/C9/C14:1-OH | 0.80921 | 7.6516E−5 |
| Met-SO/C9/C10:2 | 0.80132 | 1.4739E−4 |
| PC ae C30:2/C9/C10:2 | 0.79342 | 2.3424E−4 |

FIG. 15: Identification of specific subtypes of breast cancer using the metabolites depicted in Table 13. ROC curve analysis showing the identification of patients with Triple Negatives (n=10) and HER2-Positive/Luminals A/B (Other Tumors n=49). AUC=0.875 (95% CI: 0.762-0.98), Sensitivity=83.33%, Specificity=85.96%, Positive predictive value=55.56%%, Negative predictive value=96.08%, p-value<0.001 (1000 permutations).

TABLE 13

List of metabolites used in the Multivariate
Analysis to identify Triple Negative Tumors.

| Metabolites | AUC | pValue |
| --- | --- | --- |
| NOS Act*/C12/C10/lysoPC a C20:3 | 0.89388 | 6.193E−5 |
| NOS Act/C12/C10/PC ae C42:0 | 0.89388 | 1.7304E−5 |
| NOS Act/C12/C10/PC aa C38:3 | 0.89184 | 5.94E−5 |

*NOS Act = ratio of Citrulline/Arginine (Nitric Oxide Synthase Activity)

The above data show that it is possible to discriminate between certain types of breast cancer tumors on the basis of biomarkers, which are specific for this tumor, with high accuracy and reliability, as determined by the parameters of specificity, sensitivity, PPV and NPV.

INDUSTRIAL APPLICABILITY

The present invention makes it possible to screen subjects, in particular human patients, potentially suffering from breast cancer as well as diagnosing breast cancer in subjects in an improved manner, thereby providing for more accurate, reliable and effective screening and diagnosing procedures.

Moreover, the present invention allows for more predicting whether a patient suffering from breast cancer is likely to respond to chemotherapy, such as neoadjuvant chemotherapy, already in an early stage of the disease. In fact, the biomarkers according to the invention are easily detectable in blood, and their level is consistently related to the stage of breast cancer. Thus, the methods of the invention can easily be performed in high-throughput in a short period of time and thus allow for improved patient's compliance.

In addition, it is possible with the biomarkers and biomarker sets of the present invention to discriminate subtypes of tumors, thus allowing for an individual treatment based on the tumor subtype, thereby additionally increasing the patient's compliance, and improving success of therapy.

Further, the invention allows the determination of tumor activity by way of metabolic biomarkers, which is advantageous and superior compared to tumor characterisation as performed in the art. Assessing biochemical reflection of breast cancer tumor activity provides a suitable tool for adapting and adjusting the patient's therapy, thereby greatly increasing the patient's compliance and life quality.

Based thereon it is possible to prepare a kit being suitable to be of assistance in screening and diagnosing breast cancer, classifying the patient's tumor and determining its biochemical activity, monitoring disease progression and the patient's therapeutic response to neoadjuvant chemotherapy.

EMBODIMENTS

The present invention thus relates to the following preferred embodiments:

1. Use of a combination of metabolites contained in a blood sample of a mammalian subject, the combination of metabolites comprising at least
   (a) one amino acid selected from glutamine, glutamate and serine, and one lipid, or
   (b) glutamine and glutamate,
as a biomarker set for screening and/or diagnosing breast cancer.

2. Use according to embodiment 1, wherein the lipid is selected from arachidonic polyunsaturated phosphatidylcholine acyl-alkyl, arachidonic mono-unsaturated phosphatidylcholine acyl-alkyl and arachidonic saturated phosphatidylcholine acyl-alkyl.

3. Use according to embodiment 1 or 2, the combination of metabolites further comprising one or more of a sphingomyelin and glutaconyl carnitine.

4. Use of a combination of metabolites contained in a blood sample of a mammalian subject, the combination of metabolites comprising at least one amino acid selected from serine and glutamine,
   methylated arginine,
   one acyl carnitine and
   one lipid
as a biomarker set for prediction of therapeutic response to breast cancer neoadjuvant chemotherapy.

5. Use according to embodiment 4, wherein the acyl carnitine is selected from one or more of glutaryl carnitine and methylglutaryl carnitine.

6. Use according to embodiment 4 or 5, wherein the lipid is selected from phosphatidylcholine acyl-alkyl C44:6, phosphatidylcholine acyl-alkyl C44:5, phosphatidylcholine acyl-acyl C38:4, phosphatidylcholine acyl-alkyl C30:0, phosphatidylcholine acyl-alkyl C32:2, phosphatidylcholine acyl-alkyl C30:0, phosphatidylcholine acyl-alkyl C42:0, lysophosphatidylcholine a C17:0, lysophosphatidylcholine a C26:0, lysophosphatidylcholine a C30:0 and lysophosphatidylcholine a C24:0.

7. Use according to any one of embodiments 4 to 6, the combination of metabolites further comprising one or more of putrescine, spermine and dimethylated arginine.

8. Use of a combination of metabolites contained in a blood sample of a mammalian subject, the combination of metabolites comprising at least
one amino acid selected from glutamate, glutamine, alanine, glycine, serine and aspartate, and
one lipid
as a biomarker set for assessing biochemical reflects of breast cancer tumor activity.

9. Use according to embodiment 8, wherein the lipid is selected from phosphatidylcholine acyl-alkyl and phosphatidylcholine acyl-acyl.

10. Use according to embodiment 8 or 9, the combination of metabolites further comprising one or more of leucine and ornithine.

11. Use of a combination of metabolites contained in a blood sample of a mammalian subject, the combination of metabolites comprising at least
one acylcarnitine containing at least 10 carbon atoms in the molecule, and
one lipid containing a maximum of 3 unsaturations in the molecule as a biomarker set for subclassification of breast cancer tumor subtypes.

12. Use according to embodiment 11, wherein the lipids are selected from phosphatidylcholine acyl-acyl C38:3, phosphatidylcholine acyl-acyl C36:0, phosphatidylcholine acyl-acyl C42:0, phosphatidylcholine acyl-acyl C38:0, phosphatidylcholine acyl-alkyl C38:1, phosphatidylcholine acyl-acyl C38:2 and phosphatidylcholine acyl-alkyl C40:1.

13. Use according to embodiment 11 or 12, the combination of metabolites further comprising one or more of methionine sulfoxide, lysine, histidine, lysoPC a C24:0, lysoPC a C20:3, citruline and arginine.

14. A method for screening and/or diagnosing breast cancer in a mammalian subject, the method comprising measuring in a blood sample obtained from the subject the amount of at least
(a) one amino acid selected from glutamine, glutamate and serine, and one lipid, or
(b) glutamine and glutamate.

15. A method for prediction of therapeutic response to breast cancer neoadjuvant chemotherapy in a mammalian subject, the method comprising measuring in a blood sample obtained from the subject the amount of at least
one amino acid selected from serine and glutamine,
methylated arginine,
one acyl carnitine, and
one lipid.

16. A method for assessing the biochemical reflects of breast cancer tumor activity in a mammalian subject, the method comprising measuring in a blood sample obtained from the subject the amount of at least
one amino acid selected from glutamate, glutamine, alanine, glycine, serine and aspartate, and
one lipid.

17. A method for subclassification of breast cancer tumor subtypes in a mammalian subject, the method comprising measuring in a blood sample obtained from the subject the amount of at least
one acylcarnitine containing at least 10 carbon atoms in the molecule, and
one lipid containing a maximum of 3 unsaturations in the molecule.

18. The method according to any one of embodiments 14 to 17, wherein the measurement is based on a quantitative analytical method, preferably chromatography, spectroscopy, and mass analyzers/spectrometry.

19. The method according to embodiment 18, wherein chromatography comprises GC, CE, LC, HPLC, and UHPLC; spectroscopy comprises UV/Vis, IR, NIR and NMR; and mass analyzers/spectrometry comprises ESI, Quadrupole Mass Analyzers, Ion Trap Mass Analyzers, TOF (Time of Flight) Mass Analyzer, Orbitrap mass analyser, Magnetic Sector Mass Analyzer, Electrostatic Sector Mass Analyzer, Ion Cyclotron Resonance (ICR) and combinations thereof, including single quadrupole (Q) and triple quadrupole (QqQ), QqTOF, TOF-TOF, Q-Orbitrap, APCI-QqQ, APCI-QqTOF, MALDI-QqQ, MALDI-QqTOF, and MALDI-TOF-TOF.

The invention claimed is:

1. A method for treating a human patient for breast cancer, comprising:
receiving a blood sample from said human patient, said human patient being diagnosed with breast cancer;
analyzing said blood sample to detect a presence and amount for a combination of metabolites, wherein said combination of metabolites comprises at least glutamine and a lipid, wherein said lipid is selected from sphingolipid and glycerolipids, wherein said combination of metabolites are measured based on a quantitative analytical method chosen from chromatography, spectroscopy, and mass analyzers/spectrometry;
measuring a ratio of said combination of metabolites;
comparing at least said measured ratio to known measurements from individuals diagnosed with breast cancer, said known measurements being other measured ratios of said combination of metabolites from other samples taken from said individuals diagnosed with breast cancer;
determining, based on the comparison, at least whether said human patient is likely to respond positively to neoadjuvant chemotherapy, said positive response comprising at least whether said human patient is likely to reach complete pathological response (pCR); and
administering neoadjuvant chemotherapy to said human patient when said determination indicates that doing so to said human patient will result in pCR.

2. The method according to claim 1, further comprising the step of determining, based on the comparison, enzymatic activity of a tumor in said human patient, said enzymatic activity being used to determine whether said human patient is likely to respond positively to neoadjuvant chemotherapy.

3. The method according to claim 1, wherein said comparison step is further used to determine a type of neoadjuvant chemotherapy that should be used to treat said breast cancer in said human patient.

4. The method according to claim 1, wherein said comparison step is further used to determine a dosage of neoadjuvant chemotherapy that should be used to treat said breast cancer in said human patient.

5. The method according to claim 1, wherein said comparison step is further used to determine whether radiation should be used to treat said breast cancer in said human patient.

6. The method according to claim 1, wherein said comparison step is further used to determine whether hormone therapy should be used to treat said breast cancer in said human patient.

7. The method according to claim 1, wherein said step of determining further comprises determining, based on the comparison, a tumor subtype from a plurality of tumor subtypes.

8. The method according to claim 1, wherein said combination of metabolites are normalized before said step of measuring said ratio of said combination of metabolites.

9. The method according to claim 8, wherein said normalization is accomplished using at least a log-transformation on said combination of metabolites.

10. A method for assessing a human patient diagnosed with breast cancer, comprising:
    analyzing a blood sample from said human patient to quantify a plurality of metabolites, wherein said plurality of metabolites comprises at least glutamine and at least one lipid, wherein said at least one lipid is selected from sphingolipid and glycerolipids, wherein said plurality of metabolites are measured based on a quantitative analytical method chosen from chromatography, spectroscopy, and mass analyzers/spectrometry;
    measuring at least a ratio of said plurality of metabolites;
    comparing at least said measured ratio to known measurements from individuals suffering from breast cancer, said known measurements being other measured ratios of said plurality of metabolites from other samples taken from said individuals suffering from breast cancer;
    determining, based on the comparison, at least whether said human patient is likely to respond positively to neoadjuvant chemotherapy, said positive response comprising at least whether said human patient is likely to reach complete pathological response (pCR); and
    administering neoadjuvant chemotherapy to said human patient when said determination indicates that doing so to said human patient will result in pCR.

11. The method according to claim 10, wherein said step of determining further comprises determining, based on the comparison, enzymatic activity of a tumor in said human patient.

12. The method according to claim 11, wherein said determination of whether said human patient is likely to respond positively to neoadjuvant chemotherapy is further based on said enzymatic activity of said tumor.

13. The method according to claim 10, wherein said comparison step is further used to determine a type of neoadjuvant chemotherapy that should be used to treat said human patient.

14. The method according to claim 10, wherein said comparison step is further used to determine a dosage of neoadjuvant chemotherapy that should be used to treat said human patient.

15. The method according to claim 10, wherein said comparison step is further used to determine whether radiation should be used to treat said human patient.

16. The method according to claim 10, wherein said comparison step is further used to determine whether hormone therapy should be used to treat said human patient.

17. The method according to claim 10, further comprising the step of identifying, based on the comparison, a tumor subtype from a plurality of tumor subtypes.

18. The method according to claim 10, wherein said plurality of metabolites are normalized before said step of measuring is performed.

19. The method according to claim 18, wherein said normalization is accomplished using at least a log-transformation of at least said glutamine and said at least one lipid.

20. A method for assessing a human patient having breast cancer, comprising:
    receiving a blood sample from said human patient;
    analyzing said blood sample to detect a presence and amount for a combination of metabolites, wherein said combination of metabolites comprises at least glutamine and a lipid, wherein said lipid is selected from sphingolipid and glycerolipids, wherein said combination of metabolites are measured based on a quantitative analytical method chosen from chromatography, spectroscopy, and mass analyzers/spectrometry;
    measuring a ratio of said combination of metabolites;
    comparing at least said measured ratio to known measurements from at least individuals diagnosed with breast cancer, said known measurements being other measured ratios of said combination of metabolites from other samples taken from said individuals diagnosed with breast cancer;
    determining, based on the comparison, at least whether said human patient is likely to respond positively to chemotherapy, said positive response comprising at least whether said human patient is likely to reach complete pathological response (pCR); and
    administering chemotherapy to said human patient when said determination indicates that doing so to said human patient will result in pCR.

* * * * *